(12) United States Patent
Lee et al.

(10) Patent No.: US 11,614,427 B2
(45) Date of Patent: *Mar. 28, 2023

(54) WAVEGUIDE USABLE FOR NON-DESTRUCTIVE EVALUATION OF SPECIMEN INCLUDING WOODEN SPECIMEN

(71) Applicant: VOLT HOLDINGS LIMITED, Auckland (NZ)

(72) Inventors: Yishi Lee, Littleton, CO (US); Wayne Hall, Denver, CO (US)

(73) Assignee: VOLT HOLDINGS LIMITED, Auckland (NZ)

(*) Notice: Subject to any disclaimer, the term of this patent is extended or adjusted under 35 U.S.C. 154(b) by 128 days.

This patent is subject to a terminal disclaimer.

(21) Appl. No.: 17/008,204

(22) Filed: Aug. 31, 2020

(65) Prior Publication Data
US 2020/0400621 A1    Dec. 24, 2020

Related U.S. Application Data

(63) Continuation-in-part of application No. 16/518,789, filed on Jul. 22, 2019, now Pat. No. 11,467,132.
(Continued)

(51) Int. Cl.
*G01N 29/24* (2006.01)
*G01N 33/46* (2006.01)
(Continued)

(52) U.S. Cl.
CPC ....... *G01N 29/2462* (2013.01); *G01N 29/043* (2013.01); *G01N 29/045* (2013.01);
(Continued)

(58) Field of Classification Search
CPC .. G01N 29/2462; G01N 29/04; G01N 29/043; G01N 29/226; G01N 29/28;
(Continued)

(56) References Cited

U.S. PATENT DOCUMENTS 3,877,294 A    4/1975  Shaw
4,059,988 A    11/1977 Shaw
(Continued)

FOREIGN PATENT DOCUMENTS

| CN | 107144635 B | 11/2019 |
| WO | 02/29398 A1 | 4/2002 |
| WO | 2017125730 A1 | 7/2017 |

*Primary Examiner* — Helen C Kwok

(57) ABSTRACT

Non-limiting examples of the present disclosure relate to devices, systems and methods of manufacture for an exemplary waveguide usable for acoustic signal transmission for non-destructive evaluation (NDE) of a specimen (e.g., a wooden specimen) as well as apparatuses usable therewith. An exemplary waveguide comprises a mating portion for interfacing with a transducer horn of an ultrasonic transducer. The mating portion comprises at least a contact well configured to enable a connection between the transducer horn and the waveguide. The waveguide further comprises a body portion that comprises an upper body portion, that has a flat-faced distal end that is usable to establish contact with a surface of the specimen, and a lower body portion that is attached to and extends outwardly from the upper body portion and is further attached to the mating portion. Other technical examples are further described in the present disclosure.

20 Claims, 17 Drawing Sheets

Related U.S. Application Data

(60) Provisional application No. 62/737,405, filed on Sep. 27, 2018.

(51) Int. Cl.
   *G01N 29/28* (2006.01)
   *G01N 29/22* (2006.01)
   *G01N 29/04* (2006.01)
   *G01N 29/42* (2006.01)
   *G01N 29/34* (2006.01)

(52) U.S. Cl.
   CPC ......... *G01N 29/221* (2013.01); *G01N 29/226* (2013.01); *G01N 29/28* (2013.01); *G01N 29/348* (2013.01); *G01N 29/42* (2013.01); *G01N 33/46* (2013.01); *G01N 2291/0238* (2013.01)

(58) Field of Classification Search
   CPC .. G01N 29/07; G01N 29/2481; G01N 29/045; G01N 29/11; G01N 29/221; G01N 29/348; G01N 29/42; G01N 33/46
   See application file for complete search history.

(56) References Cited

U.S. PATENT DOCUMENTS

| | | | | |
|---|---|---|---|---|
| 4,201,093 | A | 5/1980 | Logan | |
| 4,350,044 | A * | 9/1982 | Richardson | G01N 29/11 73/632 |
| 5,285,688 | A * | 2/1994 | Robbins | G01N 29/14 73/587 |
| 5,621,172 | A * | 4/1997 | Wilson | G01N 29/348 73/579 |
| 5,760,308 | A * | 6/1998 | Beall | G01N 29/07 73/598 |
| 6,496,136 | B1 | 12/2002 | Mucciardi | |
| 6,813,927 | B1 * | 11/2004 | Harris | G01N 33/46 73/12.09 |
| 6,813,948 | B1 * | 11/2004 | Rinn | G01N 29/045 73/602 |
| 8,322,221 | B1 | 12/2012 | Sathish et al. | |
| 2004/0069064 | A1 * | 4/2004 | Blodgett | G10K 11/002 702/56 |
| 2004/0107773 | A1 | 6/2004 | Dunegan | |
| 2004/0245469 | A1 | 12/2004 | Favro et al. | |
| 2005/0005699 | A1 * | 1/2005 | Huang | G01N 29/045 73/12.09 |
| 2005/0160819 | A1 * | 7/2005 | Wang | G01N 33/0098 73/632 |
| 2006/0028345 | A1 | 2/2006 | Lee | |
| 2007/0040476 | A1 * | 2/2007 | Statnikov | C21D 7/04 310/323.18 |
| 2007/0046289 | A1 | 3/2007 | Troxler | |
| 2008/0255806 | A1 * | 10/2008 | Sambuelli | G01N 3/30 702/183 |
| 2014/0069192 | A1 | 3/2014 | Bartuli et al. | |
| 2018/0321021 | A1 | 11/2018 | Teig et al. | |
| 2019/0017896 | A1 * | 1/2019 | Whelan | G01M 5/0033 |
| 2020/0107114 | A1 | 4/2020 | Lee et al. | |
| 2020/0158695 | A1 * | 5/2020 | Hall | G01N 29/34 |
| 2020/0348266 | A1 * | 11/2020 | Ouis | G01N 29/348 |
| 2020/0400621 | A1 | 12/2020 | Lee et al. | |
| 2021/0093341 | A1 * | 4/2021 | Baker | A61B 17/22012 |

* cited by examiner

600

800
802

900 →
902

1400

1500

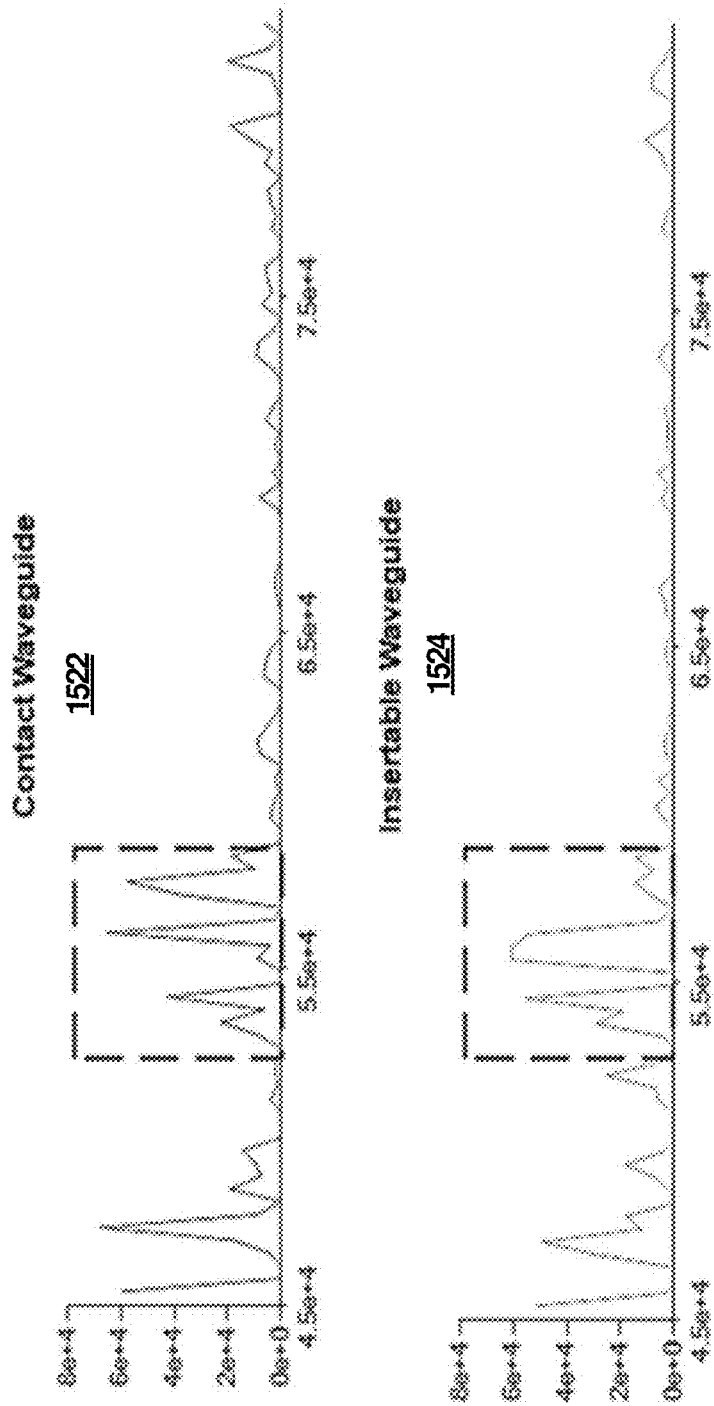

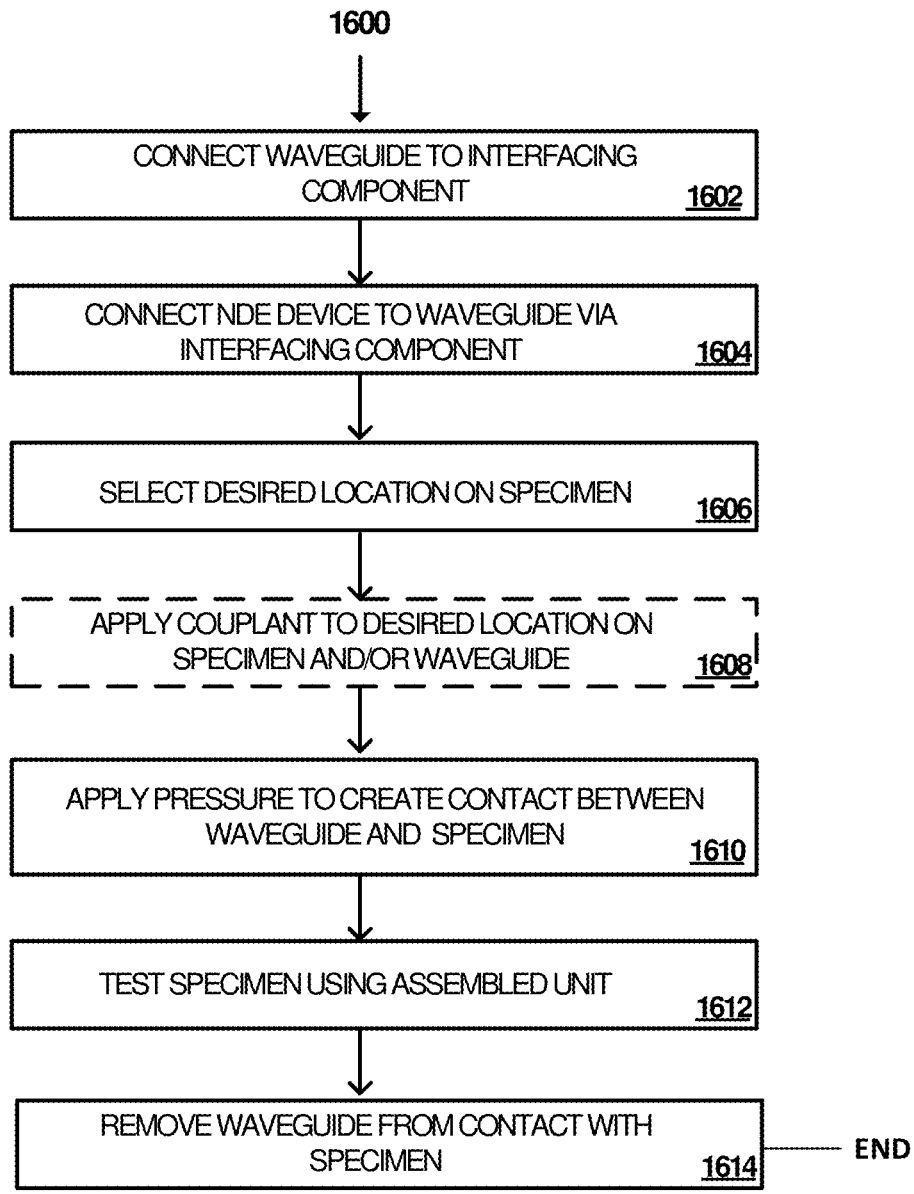

WAVEGUIDE USABLE FOR NON-DESTRUCTIVE EVALUATION OF SPECIMEN INCLUDING WOODEN SPECIMEN

CROSS-REFERENCE TO RELATED APPLICATIONS

This application is a continuation-in-part of and claims priority to U.S. Non-Provisional application Ser. No. 16/518,789 filed Jul. 22, 2019 and titled "INSERTABLE WAVEGUIDE TO IMPROVE ACOUSTIC SIGNAL TRANSMISSION IN WOODEN SPECIMEN", and further claims priority to U.S. Provisional Application No. 62/737,405, filed Sep. 27, 2018 and titled "INSERTABLE WAVEGUIDE TO IMPROVE ULTRASONIC TRANSMISSION THROUGH UTILITY POLE", both of which are hereby incorporated by reference herein in its entirety.

TECHNICAL FIELD

The present disclosure relates to devices, systems and methods capable of producing and receiving acoustic signals in the area of non-destructive evaluation (NDE), where the acoustic signals may be utilized to assess structural integrity of specimen such as a wood specimen.

BACKGROUND

The aging infrastructure power distribution grids across the world demands a rigorous and an objective monitoring process to assess structural integrity of hundreds of millions of wooden utility poles. Current inspection methodologies are antiquated and either lack the ability to provide truly accurate evaluations and/or result in compromising the structural integrity of a utility pole. For instance, one commonly utilized method of evaluating utility poles is an inspectors' visual evaluation of the pole. Visual inspection may be able to identify some structural integrity issues but is not a true indicator of whether the utility pole is experiencing incipient decay internally. As an example, a utility pole may appear to be fine, where an inspector gives the utility pole a passing grade, but internal decay may significantly affect the longevity of the pole, sometimes cutting its lifetime by decades. As there may be long gaps between the times when a utility pole is inspected, it is paramount to accurately assess the structural integrity of the utility pole.

Alternative measures for inspecting utility poles include drilling into the utility pole and testing a wood sample from its core. While this may provide more a reliable indication of whether a utility pole is experiencing decay, as compared with visual inspection, drilling into the core of a utility pole compromises the structural integrity of the pole. For instance, utility poles are coated with a protective layering that helps minimize exposure to elements that expedite decay. If this protective layering is compromised, decay can be expedited due to exposure to elements of nature, bacteria, etc.

Additional concerns exist when new technology is integrated in a field that commonly uses such antiquated methods to evaluate structural integrity. For instance, usage of complex electronic equipment may pose training challenges for inspectors and result in human error during actual operation as complex operating environments can be created.

Furthermore, there are technical complications when considering the application of acoustic signals to evaluate a wooden structure such as a wooden utility pole. For instance, a component is needed to transmit an acoustic signal through the wooden specimen. That component needs to be insertable into the wooden specimen, common examples of which are nails and screws. However, commercial off-the-shelf metal nails/screws are designed for hardware purposes and not as a transmission carrier for acoustic signals. For instance, a resonance frequency of a commercial off-the-shelf metal nail/screw is not tuned for accurate transmission of acoustic signals. This raises the likelihood of receiving inaccurate readings if a commercial off-the-shelf metal nail/screw is used as a component to transmit an acoustic signal through the wooden specimen. Resonance issues become greater when commercial off-the-shelf metal nails/screws are threaded and not flat and uniform. For instance, a commercial off-the-shelf metal nail/screw that is threaded can create greater resonance variance leading to distorted signal reading that may affect an inspection of a wooden specimen.

Additional complications arise when an inspector uses commercial off-the-shelf metal nails/screws for inspection of a wooden specimen. As an example, an inspector may hammer an ordinary nail into the wooden specimen. The resulted force of hammering a nail into the wooden specimen may result in damage or deformation of a nail head. The damaged surface impedes sound propagation and introduces uncontrollable variations during transmission, which can greatly impact inspection results.

For these and other reasons, the present disclosure is presented to greatly advance the technical field of testing of structural integrity of wooden structures.

SUMMARY

In view of the foregoing technical challenges, non-limiting examples of the present disclosure relate to devices, systems and methods of manufacture for an exemplary waveguide that is usable for acoustic signal transmission for non-destructive evaluation (NDE) of a specimen such as a wooden specimen. Among other technical benefits, the waveguide is designed and configured to: resonate at a predetermined frequency to provide energy transmission and reception of acoustic signals (e.g., ultrasonic/ultrasound); optimize signal transmission therethrough including reduction in attenuation of transmitted ultrasonic signals; provide an intuitive and protective design that enhances usage of the waveguide for non-destructive evaluation of a specimen as well as enables the waveguide to seamlessly integrate with other devices, components etc. An exemplary waveguide comprises a mating portion for interfacing with a transducer horn of an ultrasonic transducer or the like. The mating portion comprises a contact well and may further comprise an impact surface. The contact well is utilized to connect the waveguide to a transducer horn. The waveguide further comprises a body portion that comprises an upper body portion, that has a flat-faced distal end that is usable to establish contact with a surface of the specimen, and a lower body portion that is attached to and extends outwardly from the upper body portion and is further attached to the mating portion. In some examples, an exemplary upper body portion may be fabricated in a manner that does not require the upper body portion to be driven into a wooden specimen. For example, a user of an NDE device may apply pressure (e.g., manually or via a mechanical device) to the NDE device that is attached to the waveguide, thereby enabling the waveguide to contact the wooden specimen. An exemplary upper body portion of a waveguide may be fabricated in any shape including but not limited to shapes such as: circular, square, rectangular, hexagonal, triangular or any other cross-sectional geometries. Further non-limiting examples describe an interfacing component for securing one or more devices to the waveguide as well as an extraction component that is configured to minimize damage to the waveguide during extraction when the waveguide comprises a radiating component that is shallowly driven into a wooden specimen. Additional non-limiting examples describe methods of manufacturing NDE components described herein.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Additional aspects, features, and/or advantages of examples will be set forth in part in the description which follows and, in part, will be apparent from the description, or may be learned by practice of the disclosure.

BRIEF DESCRIPTION OF THE DRAWINGS

Non-limiting and non-exhaustive examples are described with reference to the following figures.

FIGS. 15A and 15B illustrate comparative graphing providing a signal comparison between exemplary waveguide designs that penetrate a specimen and exemplary waveguide designs that contacts a specimen without penetrating the specimen, with which aspects of the present disclosure may be practiced.

FIG. 16 illustrates an exemplary method pertaining to usage of an exemplary waveguide for NDE of a specimen, with which aspects of the present disclosure may be practiced.

DETAILED DESCRIPTION

Figure 1:
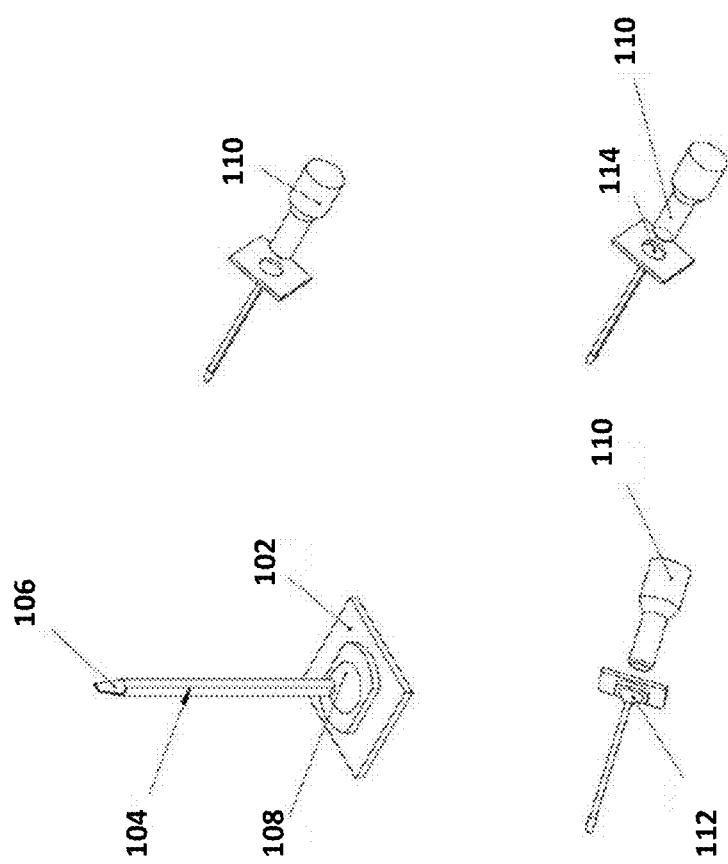
FIG. 1 illustrates an exploded view providing non-limiting examples of a waveguide, with which aspects of the present disclosure may be practiced.

Non-limiting examples of the present disclosure relate to devices, systems and methods of manufacture for an exemplary waveguide that is usable for acoustic signal transmission for NDE of a specimen such as a wooden specimen. Among other technical benefits, the waveguide is designed and configured to: resonate at a predetermined frequency to provide energy transmission and reception of acoustic signals (e.g., ultrasound); optimize signal transmission therethrough including reduction in attenuation of transmitted acoustic signals; provide an intuitive and protective design that enhances usage of the waveguide for non-destructive evaluation of specimen (e.g., wooden specimen) as well as enables the waveguide to seamlessly integrate with other devices, components etc. As indicated in the foregoing a non-limiting example of a specimen is a wooden specimen such as a wooden utility pole. However, examples described herein may pertain to NDE of any type of wooden specimen including but not limited to wooden cylinders such as wooden utility poles, pilings and logs, among other examples. It is further to be understood that novelty of the present disclosure also extends to specimen/structures comprising other types of materials through modifications that are recognized by one skilled in the field of art. For instance, an exemplary waveguide may be usable to execute NDE on other types of specimen including but not limited to metals, woods, glass, plastics and ceramics, among other examples. In such instances, a waveguide can be fabricated and/or tuned to resonate a predetermined frequency that is optimal for energy transmission of acoustic waves through specific types of specimen. For ease of explanation, an exemplary specimen will be subsequently referenced as a wooden specimen.

When being implemented, one or more NDE devices, attached to a wooden specimen, are configured to transmit and/or receive acoustic signals, via an exemplary waveguide. This enables NDE to be executed on the wooden specimen. Non-limiting examples of acoustic signals comprise but are not limited to ultrasonic waves/ultrasonic signal data. Ultrasonic signals are referenced throughout the description for convenience. However, it is to be understood that the present disclosure may work with any type of acoustic signal.

In addition to the technical benefits identified above, an exemplary waveguide is designed and fabricated to allow acoustic signals (e.g., ultrasonic waves) to contact a wooden specimen regardless of the surface conditions of the wooden specimen. In some technical examples, contact with a wooden specimen pertains to instances where the waveguide is guided into/penetrates the wooden specimen. In other technical examples, contact with a wooden specimen pertains to instances where the waveguide touches (literally contacts) a surface of the wooden specimen without actually penetrating the wooden specimen. Depending on how the waveguide contacts the wooden specimen (e.g., driven into or contacting an outer portion thereof) can affect the type of signal that is received. However, the waveguide is designed and fabricated to resonate at a predetermined frequency that is optimal for energy transmission of acoustic waves regardless of how the waveguide contacts a wooden specimen, where signal waves can be analyzed for the type of contact made to obtain a best possibly reading during NDE. This overcomes the technical challenges presented when trying to utilize to ordinary nails/screws to conduct NDE evaluation of wooden structures. In some examples, an exemplary waveguide may comprise a radiating portion/component that is interchangeable. For example, a user may be able to switch out a radiating portion depending on whether the conditions are optimal for a specific kind of contact or even if multiple different types of NDE are to be executed.

Additional advantages of the waveguide overcome technical challenges in the field of NDE of specimen such as wooden specimen (e.g., wooden utility poles). For instance, an exemplary waveguide is designed and fabricated to comprise a protected mating portion that mitigates any deformation or damage to the waveguide that may affect transmission of acoustic signals therethrough, for example, resulting from impact that secures the waveguide into a wooden specimen or the application of force to an NDE device/attached waveguide that contacts a wooden specimen. In examples where an upper body portion of the waveguide is designed to shallowly penetrate a wooden specimen for NDE, an exemplary waveguide may further be fabricated to provide a depth indicator on a radiating component to control insertion depth of the waveguide. This may provide inspectors with a visual indication of how deep to insert the waveguide into the wooden specimen as well as mitigate damage to the wooden specimen that may result from puncturing the wooden specimen too deeply.

Furthermore, an exemplary waveguide provides structural support for attached devices that may be utilized for inspection purposes. For instance, a novel design of the waveguide enables devices to be attached to both a transducer and a specimen (e.g., wooden specimen) the waveguide to execute NDE of a wooden specimen. Non-limiting examples of such devices comprise but are not limited to ultrasonic sensors; transducers; NDE devices for testing of wooden specimen (e.g., wooden structures); coupling interfacing components; extraction components; mechanical support devices for securing handsfree contact between the waveguide and a specimen; and computing devices, among other examples.

An exemplary waveguide comprises a mating portion for interfacing with a transducer horn of an ultrasonic transducer. The mating portion may comprise contact well and/or an impact surface. In examples where both a contact well and an impact surface are present, the contact well is fabricated within the impact surface so that the contact well is not contacted during an impact that drives the waveguide into wood. In some alternative examples where a specific model of the waveguide is not to be driven into a wooden specimen, one distal end of the waveguide may be fabricated with only a contact well for establishing a connection with a transducer (e.g., ultrasonic transducer). The contact well is utilized to connect the waveguide to a transducer horn of an ultrasonic transducer or other type of device that used to generate acoustic waves for NDE of a wooden specimen. In one example, the contact well may be circular in shape to securely attach to a transducer horn of an ultrasonic transducer. However, it is to be recognized that the contact well may be fabricated in any shape to fit any type of device that is interfacing with the waveguide without departing from the spirit of the present disclosure. In alternative examples, an exemplary waveguide may be threaded to enable insertion of the waveguide into a wooden specimen without the need to use a hammer, mallet, pneumatic device.

The waveguide further comprises a body portion that extends from the mating portion to formulate a single NDE component. The body portion comprises an upper body portion (radiating component) optimized for NDE of wood and transmission of ultrasonic signal data. The upper body portion is configured to make contact with a wooden specimen, and a lower body portion that is attached to and extends outwardly from the upper body portion and is attached to the mating portion. The lower body portion may be a shank portion that guides an acoustic wave (ultrasonic wave), from an attached transducer via the contact well, to the radiating component for transmission and receipt of wave signals through the wooden specimen. This configuration optimizes propagation of ultrasonic waves through the contact well into the wooden specimen through the body of the waveguide. An exemplary body portion and/or mating portion of a waveguide may be fabricated in any shape including but not limited to shapes such as: circular, square, rectangular, hexagonal, triangular or any other cross-sectional geometries. In some non-limiting examples where an upper body portion is designed to be driven into a wooden specimen, a diameter of the upper body portion of the radiating component is smaller than a diameter of the lower body portion. This configuration minimizes the intrusion of the waveguide into the wooden specimen as well as creates a visual depth indicator, at an intersection between the upper body portion and the lower body portion, for driving the radiating component into the wooden specimen. This helps inspectors drive the waveguide into the wooden specimen only as much as necessary to optimize propagation of ultrasonic signal data through the wooden specimen while minimizing impact to structural integrity of the wooden specimen. In some examples, the upper body portion and the lower body portion are both cylindrical in shape. In other examples, an upper body portion is flat-faced (e.g., having a flat-faced distal end) having a distal end that is usable to establish contact with a surface of the wood specimen. The upper body portion may have a larger diameter than a lower body portion of a waveguide to thereby increase the contact area with the wooden specimen. In turn, this fabricated configuration amplifies the transmission and reception of an ultrasonic signal for NDE. However, it is to be recognized that the entire body of the waveguide is designed and fabricated for optimal NDE evaluation as the entire body resonates during transmission and receipt of ultrasonic signal data.

As referenced in the foregoing description, a modified waveguide design is presented that comprises an upper body portion (radiating portion/component) fabricated to enable contact with a wooden specimen without requiring the upper body portion to be driven into/penetrate the wooden specimen. This helps minimize the risk of causing additional damage/decay to a wooden specimen during NDE. In such modified examples, a user may apply an appropriate amount of pressure (e.g., 5 or more pounds of pressure) to an NDE device, which is attached with the waveguide, while contacting a wooden specimen. In some alternative examples, the modified waveguide design enables a handsfree approach to establish contact between a waveguide and a wooden specimen. For instance, an adhesive may be applied to the waveguide and/or a specific location on specimen to which the waveguide attaches, thereby establishing secure contact between the waveguide and the specimen for NDE. In one specific example, fabrication of the waveguide may comprise application of an activatable adhesive on an upper body portion of the waveguide. In another example, an adhesive may be mixed into a couplant that is contacting the waveguide and wooden specimen, thereby fostering secure contact between the waveguide and the wooden specimen. An exemplary couplant is configured to enhance ultrasonic energy transmission by reducing differences in acoustic impedance. In yet another alternative example, an apparatus may be used to stabilize an assembled unit (NDE device attached to waveguide via an interfacing component) to the surface of the specimen and thereby provide handsfree capability with more consistent pressure as compared to a user manually holding the assembled unit against a surface of the wooden specimen. Exemplary stabilizing apparatuses may secure the assembled unit to a surface of a wooden specimen through one or more of a mechanical mechanism, an electromechanical mechanism, a pneumatic mechanism or a combination thereof.

Additional examples of the present disclosure extend to generation and implementation of an exemplary interfacing component that is utilized to secure a device (e.g., an ultrasonic transducer) to the waveguide thereby creating a handsfree configuration for an assembled unit to aid NDE of wooden specimen. In non-limiting examples, interfacing component may comprise but is not limited to components such as: a base portion formulated out of a solid and rigid material; a holding slot, fabricated within the base portion, configured to enable the interfacing component to attach to the waveguide, and an aperture at an end portion of the base portion that is configured to enable the transducer horn to contact the contact well when the interfacing component is attached to the waveguide. In alternative examples, an end portion of the base portion may comprise, instead of an aperture, a clamping component to secure devices to the waveguide, for example, in instances where a device such as an ultrasonic transducer is unthreaded. In some instances, a base portion may be minimized if the contact well is tapped and deep enough to allow a transducer horn (e.g., threaded transducer horn) to be secured to the waveguide and in contact with the contact well (e.g., through clock-wise or counter clock-wise rotation).

In further non-limiting examples, the present disclosure describes generation and implement of an extraction component that is configured for safe removal of the waveguide from the wooden specimen to mitigate damage to the waveguide upon extraction when a waveguide is driven into a wooden specimen. In non-limiting examples, the extraction component may comprise but is not limited to components such as: a base portion formulated out of a solid and rigid material; a channel fabricated in the base portion that is usable to attach the extraction component to the waveguide; and one or more extraction slots, fabricated on one or more end portions of the base portion, to enable one or more tools to be inserted into the one or more extraction slots for controlled removal of the waveguide from the wooden specimen. In some alternative examples, the extraction component may not be required to extract an exemplary waveguide. For instance, where an NDE device/waveguide contact the wooden specimen by manually applying pressure, those components can be simply removed from contact with the wooden specimen. In examples where an adhesive (e.g., small moderate amount proportionally) is applied, a proper amount of force can be applied to disengage the NDE device/waveguide from the wooden specimen. In another alternative example, a substance to dissolve the adhesive may be applied to assist with disengaging the NDE device/waveguide from the wooden specimen.

Moreover, non-limiting examples described herein extend to methods of manufacture of NDE components such as waveguides, coupling interface components and extractions components, among other examples. For instance, a method of manufacture of an exemplary waveguide may comprise selection of one or more metallic components; testing resonance frequencies of selected metallic components (e.g., metals, alloys, a combination thereof) and fabricating an exemplary waveguide. The waveguide is fabricated to generate a resonance frequency that matches a resonance frequency of an ultrasonic wave for NDE of a wooden specimen being tested such as a wooden utility pole. Also, an exemplary waveguide may be fabricated out of a material that matches a transducer horn to reduce impedance mismatch. The method of manufacture may comprise fabricating the mating portion of the waveguide as well as fabricating the body portion of the waveguide. In further examples, the coupling interface component and the extraction component are also fabricated though separately from the waveguide. Once an exemplary waveguide is fabricated, the waveguide, among other fabricated components, may be tested to ensure the waveguide is properly constructed and operating at the optimal resonance frequency for NDE of wooden specimen. As referenced in the foregoing description, some instances of fabrication of a waveguide may enable the interchanging of radiating components. For instance, the radiating component may be removable so that a user can quickly change the radiating component depending on the type of contact to be made with the wooden specimen. In one example, this may comprise twisting the radiating component to lock/unlock the radiating component from a shank portion of a waveguide. The shank portion may remain attached to a coupling flange that enables a transducer to be attached to the waveguide.

Further non-limiting examples, reference interfacing between an exemplary waveguide an NDE device that is utilized for NDE of wooden specimen. An exemplary NDE device may comprise: a transducer assembly that comprises an ultrasonic transducer; an electronic processing assembly that comprises a printed circuit assembly and a processing unit; and a casing assembly, that houses the transducer assembly and the electronic processing assembly. The casing assembly is configured, at an end portion, to attach to the waveguide, via a mating portion of the waveguide, for NDE of a wooden specimen such as a wooden cylinder or a wooden utility pole. The NDE device may be configured to receive, from the ultrasonic transducer, ultrasonic signal data and transmit, to a computing device, the ultrasonic signal data via a data transmission component of its processing unit. In additional examples described herein, multiple NDE devices may be attached to a wooden specimen, via multiple waveguides, to enable more comprehensive testing of structural integrity of a wooden specimen. For example, a first NDE device may be configured as a transmitting device, for transmitting of ultrasonic signal data, and a second NDE device may be configured as a receiving device to receive transmitted ultrasonic signal data. Data from both devices may be propagated to a computing device that may be configured to analyze the ultrasonic signal data. In further examples, an NDE application/service may be utilized to control NDE of a wooden specimen. For instance, control commands may be transmitted to check a connection between an NDE device and a waveguide or manage scientific parameters (e.g., voltage) propagated through an exemplary waveguide, among other examples.

FIG. 1 illustrates an exploded view 100 providing non-limiting examples of a waveguide, with which aspects of the present disclosure may be practiced. The examples shown in exploded view 100 provide non-limiting examples of one embodiment of a waveguide. However, it is to be understood that other embodiments of an exemplary waveguide, provided in other portions of the present disclosure, may be preferred for NDE of wooden specimen. In any example of a waveguide, and components described thereof, may be fabricated out of one or more metallic components. Non-limiting examples of metallic components comprise but are not limited to: metals (e.g., steel, brass, aluminum); alloys or a combination thereof. An exemplary metal used to manufacture a waveguide may match the metal type of an ultrasonic device (e.g., that of a transducer horn of an ultrasonic transducer) to optimize signal transmission therethrough. The waveguide may be fabricated from single piece of metal or a plurality of different pieces of metal that are forged together (e.g., soldered). An exemplary waveguide is fabricated to resonate at a predetermined frequency that is optimized for non-destructive evaluation (NDE) of a wooden specimen such as a wooden utility pole. As a non-limiting example, an exemplary waveguide is fabricated so the resonance frequency of said waveguide resonates at 50 kHz. However, it is to be understood that the waveguide can be fabricated to resonate at any desired frequency (or range of frequencies) without departing from the spirit of the present disclosure.

The waveguide shown in side view 100 comprises three main segments: a mating portion 102; a body portion 104 and an end portion 106. The mating portion 102 is configured for interfacing with a device that produces acoustic signals (e.g., ultrasonic waves). Non-limiting examples of such devices comprise an ultrasonic transducer, ultrasonic sensor etc., where a transducer horn 110 of an ultrasonic device interfaces with the mating portion 102 thereby enabling the waveguide to transmit and receive ultrasonic waves. The mating portion 102 comprises three sub-segments: an amplifying cone 108; an impact surface 112; and a contact well 114. The impact surface 112 is shaped and fabricated to receive an impact for driving the waveguide into wood (e.g., a wooden structure such as a wooden utility pole). The impact surface 112 may be a flat uniform surface that is fabricated in any shape to maximize contact between a tool (e.g., hammer) or device (pneumatic system) in order to drive the waveguide into a wood specimen. For instance, in the example shown in side view 100, the impact surface 112 is a square shape. In an alternative example shown in FIG. 4, an impact surface is fabricated in a circular shape.

The contact well 114 is utilized to connect the waveguide to a transducer horn 110 of an ultrasonic transducer or other type of device that used to generate acoustic waves for NDE of a wooden specimen. The transducer horn 110 is placed in direct contact with the contact well 114. In some examples, the contact well 114 is fabricated so that the transducer horn 110 is secured in the contact well 114. For example, the transducer horn 110 may be secured to the contact well 114 via a handheld connection or via a component connection such as a coupling interface component described herein. In one example, one or more side walls of the contact well 114 are tapped to enable a threaded connection with the transducer horn 110. In another example, the contact well 114 is secured to the transducer horn 110 via magnetic connection, where one or more of the transducer horn 110 and the contact well 114 may be magnetized to secure a connection.

During fabrication, the contact well 114 is cut into the impact surface 112 so that the contact well is protected and not compromised by the impact of driving the waveguide into the wood. For example, the contact well 114 is engraved within the impact surface 112 to protect a surface of the contact well 114 from resulting impact to the impact surface 112. That is, the contact well 114 is fabricated within a portion of the impact surface 112 (e.g., center or middle portion) so that the contact well is not contacted during an impact that drives the waveguide into wood. In such a configuration, the impact surface 112 may be elevated as compared with the contact well 114, so that the impact surface 112 receives a resulting impact when the waveguide is driven into wood.

Furthermore, the mating portion 102 may comprise an amplifying cone 108. The amplifying cone 108 is designed to focus ultrasonic energy from the contact well 114 to the body portion 104 of the waveguide. When ultrasonic waves are transmitted from the transducer horn 110, the amplifying cone 108 enhances propagation by channeling the ultrasonic energy directly to the body portion 104. In some examples of the waveguide, an amplifying cone 108 may be omitted from the design.

The body portion 104 comprises a portion of the waveguide that connects to both the mating portion 102 and the wooden specimen, for example, where a portion of the body portion 104 may be embedded with the wooden specimen by impact, rotational, force, application of pressure, etc. The body portion 104 is optimized for NDE, for example, transmission of ultrasonic wave data through the wood and receipt of ultrasonic wave data from the wood. For example, the body portion 104 comprises a linear or cylindrical portion and an end portion 106. The end portion 106 is embedded into the wooden specimen due to impact to the impact surface 112 of the mating portion 102. In the example, shown, the end portion 106 comprises a linear tip. A linear tip of the end portion 106 may increase a contact area of a portion of the waveguide that is embedded into the wooden specimen. For instance, a linear tip may radiate more ultrasonic energy than a sharp point tip of an ordinary nail. In alternative examples, the end portion 106 may comprise a cone-shaped tip that is engineered for ultrasonic energy transmission.

Figure 2:
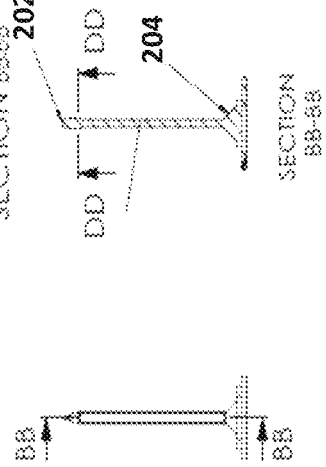
FIG. 2 illustrates a section view providing non-limiting examples of a waveguide, with which aspects of the present disclosure may be practiced.

FIG. 2 illustrates a section view 200 providing non-limiting examples of a waveguide, with which aspects of the present disclosure may be practiced. The examples shown in section view 200 provides non-limiting examples of a waveguide. However, it is to be understood that other embodiments of an exemplary waveguide, provided in other portions of the present disclosure, may be preferred for NDE of wooden specimen. Section view 200 highlights a cylindrical body portion (e.g., body portion 104 of FIG. 1) of an exemplary waveguide. In section view 200, a body portion of a waveguide is a segmented cylindrical body formed by one or more symmetrical secant cuts 202. The curved surfaces in section view 200 are denoted as contacting surfaces 204, which contact a portion of a wooden specimen that the waveguide is embedded in. The flat surfaces resulted from the secant cuts 202 are denoted as the non-contacting surfaces 206. Since the body portion of the waveguide shown in section view 200 is a segmented cylinder, only the contacting surface 204 is rested against the boundary between the waveguide and a wooden specimen. The non-contacting surface 206 on the other hand creates a gap between the waveguide and the wooden specimen to prevent any transfer of energy into the wooden specimen, which results in the Rayleigh wave mode. The segmented cylindrical body of the waveguide is enlarged into a circular base. As it extrudes outward in the direction along the body portion, the draft angle for the contacting surfaces 204 (shown in AA-AA) is greater than the draft angle for the non-contacting surfaces 206 (shown in BB-BB). The resulted circular prism forms the end portion with a linear sharp tip (or alternatively a cone-shaped tip).

Figure 3:
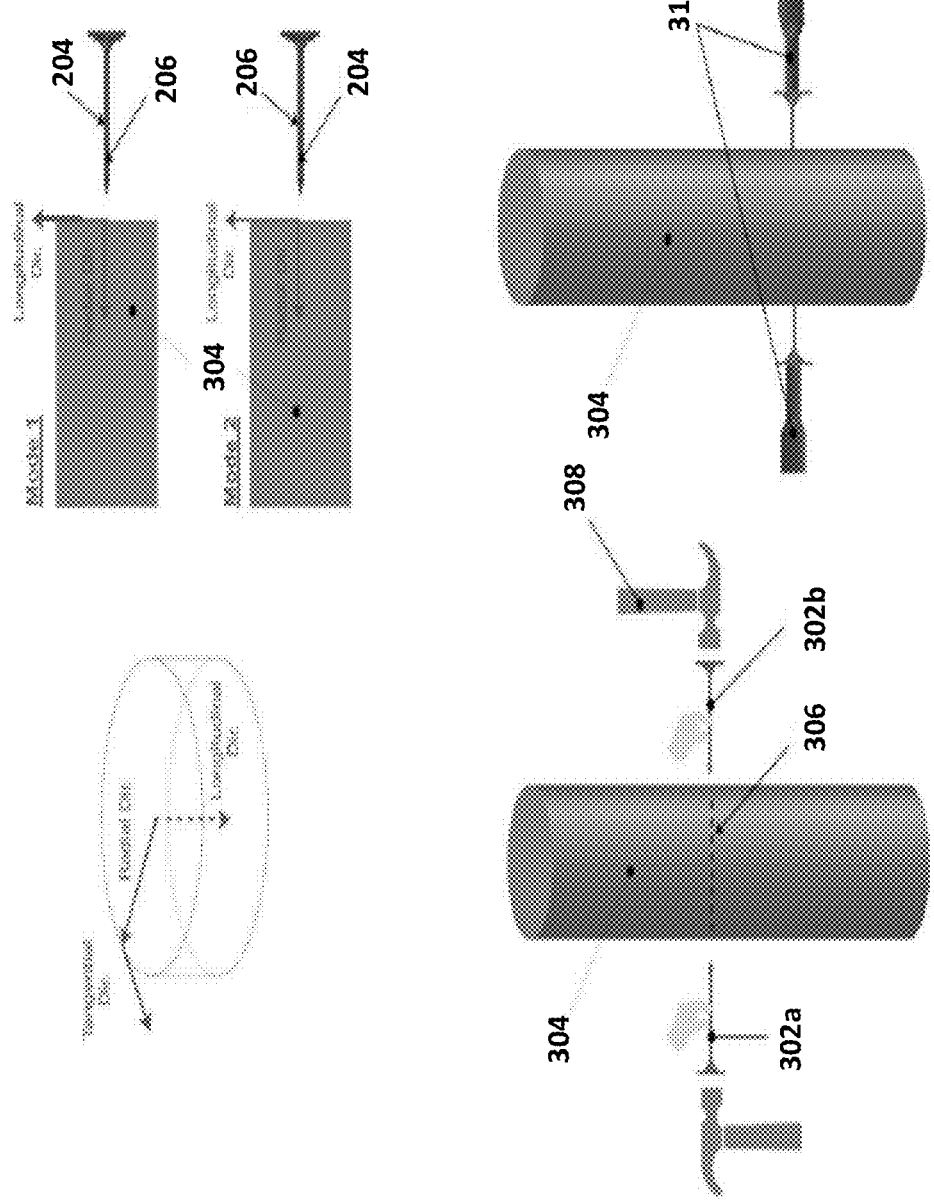
FIG. 3 illustrates a procedural diagram for insertion of a waveguide into a wooden specimen, with which aspects of the present disclosure may be practiced.

FIG. 3 illustrates a procedural diagram 300 for insertion of a waveguide into a wooden specimen, with which aspects of the present disclosure may be practiced. Procedural diagram 300 illustrates two exemplary waveguides 302a and 302b being inserted into a wooden specimen 304 (e.g., wooden cylinder, wooden utility pole). To achieve non-limiting examples of desired results, first and second modes of operation are described, where exemplary modes of operation reference interaction between waveguides, 302a and 302b, a wooden specimen 306 and mounted transducers 310, where Rayleigh wave excitation can be controlled during NDE of a wooden specimen 306 using said waveguides 302a and 302b.

A first mode of operation is described in the following steps. First, a transmitting waveguide 302a and a receiving waveguide 302b are oriented with respective end points of the body portions pointing towards the center of the wooden specimen 306. Next, each waveguide is rotated about its center axis until the non-contacting surface is perpendicular to the tangential direction of the wooden specimen 306, and the contacting surface is perpendicular to the longitudinal direction of the wooden specimen 306. Furthermore, a tool 308 (e.g., hammer or pneumatic device) is used to insert the waveguides into a wooden specimen 306 in opposite direction by gently striking an impact surface of each respective waveguide, 302a and 302b. The plane formed by the two insertion points is denoted as the examination plane 306. Moreover, ultrasonic transducers 310 are mounted to the respective waveguides by placing each transducer aperture in contact with a respective contact well of each waveguide 302a and 302b. Using the described approach, the excited Rayleigh wave only occurs at the contacting surfaces and propagates outward along the longitudinal direction without interfering with the wave propagating in the radial direction across the wooden structure 306.

When Rayleigh wave excitation is desirable in the tangential direction, a second mode of operation can be used. First, a transmitting waveguide 302a and a receiving waveguide 302b are oriented with respective end points of the body portions pointing towards the center of the wooden specimen 306. Next, each waveguide is rotated about its center axis until the contacting surface is perpendicular to the tangential direction of the wooden specimen 306, and the non-contacting surface is perpendicular to the longitudinal direction. Furthermore, a tool 308 is used to insert the waveguides into a wooden specimen 306 in opposite direction by gently striking an impact surface of each respective waveguide, 302a and 302b. Moreover, ultrasonic transducers 310 are mounted to the respective waveguides by placing each transducer aperture in contact with a respective contact well of each waveguide 302a and 302b. The second mode configuration rotates the waveguide by 90 degrees, permitting the excitation of Rayleigh wave mode in the tangential direction. Meanwhile, the orientation of the linear tip reduces radial wave propagation on the examination plane 306.

Figure 4:
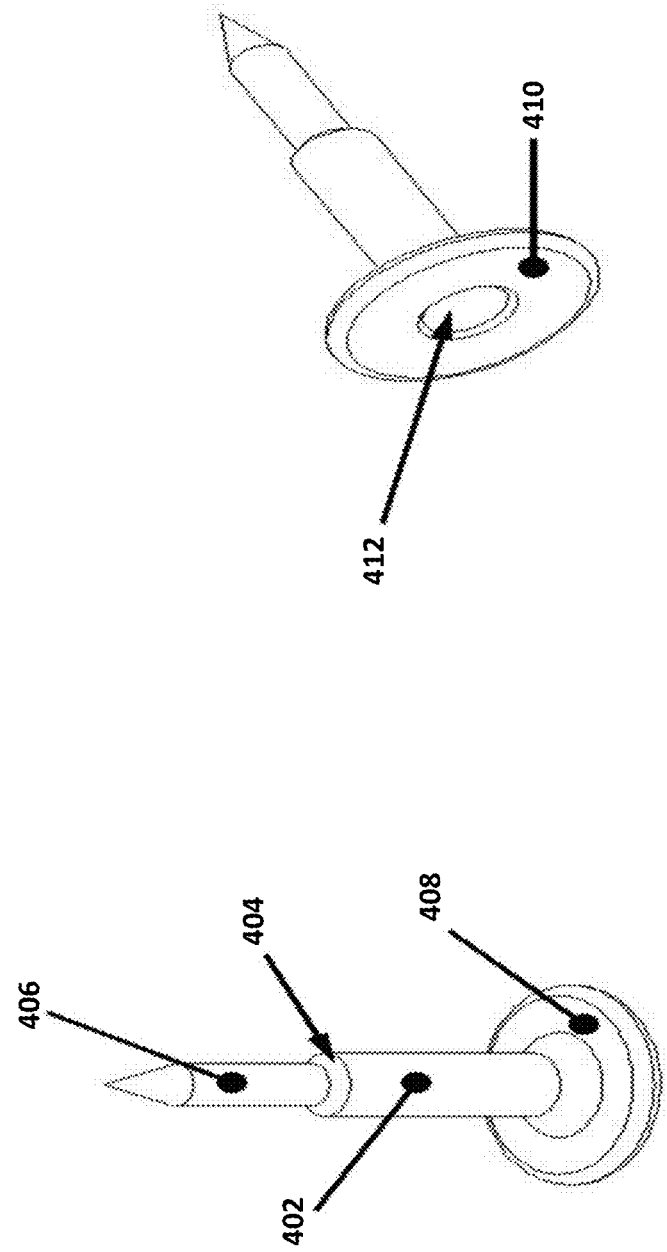
FIG. 4 illustrates side views providing non-limiting examples of a waveguide, with which aspects of the present disclosure may be practiced.

FIG. 4 illustrates side views 400 providing non-limiting examples of a waveguide, with which aspects of the present disclosure may be practiced. As described in the foregoing description, an exemplary waveguide is tuned to a resonance frequency for NDE of a wooden specimen such as a wooden utility pole. Waveguide, shown in side views 400, comprises a mating portion 408 for interfacing with a transducer horn of an ultrasonic transducer or other similar device.

The mating portion 408 comprises an impact surface 410 and a contact well 412, description of which has been provided in the foregoing description of the present disclosure. As previously indicated, the contact well 412 is fabricated within the impact surface 410 so that the contact well is not contacted during an impact that drives the waveguide into a wooden specimen. The contact well 412 is utilized to connect the waveguide to a transducer horn of an ultrasonic transducer or other type of device that used to generate acoustic waves for NDE of a wooden specimen. Through fabrication, the contact well 412 is cut into the impact surface 410 so that the contact well 412 is protected and not compromised by the impact of driving the waveguide into a wooden specimen. Side views 400 provide an illustration that emphasizes a fabricated contact well 412 and its position and elevation relative to the impact surface 410. In the example shown in side view 400, the contact well 412 is circular in shape to securely attach to a transducer horn of an ultrasonic transducer. However, it is to be recognized that the contact well 412 may be fabricated in any shape to fit any type of device that is interfacing with the waveguide without departing from the spirit of the present disclosure.

The waveguide further comprises a body portion, which is collectively represented by labeling 402-406. As shown in side view 400, the body portion extends from the mating portion 408 to formulate a single NDE component. The body portion comprises a radiating component optimized for NDE of wooden specimen, namely transmission/receipt of acoustic signal data. The radiating component comprises an upper body portion 406, that is drivable into a wooden specimen, and a lower body portion 402 that is attached to and extends outwardly from the upper body portion and is attached to the mating portion 408. This configuration optimizes propagation of ultrasonic waves through the contact well 412 into the wooden specimen via the radiating component. In some non-limiting examples, a diameter of the upper body portion 406 of the radiating component is smaller than a diameter of the lower body portion 402. This configuration minimizes the intrusion of the waveguide into the wooden specimen, as well as creates a visual depth indicator 404, at an intersection between the upper body portion 406 and the lower body portion 402, for driving the radiating component into the wooden specimen. This helps inspectors drive the waveguide into the wooden specimen only as much as necessary to optimize propagation of ultrasonic signal data through the wooden specimen while minimizing impact to structural integrity of the wooden specimen. In another example, the lower body portion 402 is thicker than the upper body portion 406, where a diameter of the lower body portion 402 tapers off from a thickest point (nearest to the mating portion 408) to a thinnest point (nearest an end point of the upper body portion 406). In further examples, the upper body portion 406 and the lower body portion 402 are cylindrical in shape. Through, it is to be recognized that any type of shape that formulates a uniform cross-section into the wooden specimen can be fabricated without departing from the spirit of the present disclosure.

Furthermore, an end portion of the upper body portion 406, furthest from the mating portion 408, may comprise a cone-shaped tip or a linear tip, among other non-limiting examples, to optimize insertion of the waveguide into wood. The end portion of the upper body portion 406 is what is driven into a wooden specimen, where an inspector may contact the impact surface 412 until the upper body portion 406 is driven into the wooden specimen up to a point of the visual depth indicator 404. In some examples, an inspector may utilize tools such as hammers, mallets, pneumatic devices or the like to apply force to the impact surface 412 to drive the waveguide into the wooden specimen. It is to be understood that an exemplary waveguide can be modified in length and/or size to optimize ultrasonic transmission at any desired resonance frequency. For instance, waveguides can be pre-fabricated at different lengths and/or sizes for evaluating different types of wooden specimen. In some alternative examples (not shown), one or more of the body portions may be adjustable during usage. In one example, a lower body portion 402 of the waveguide is extensible, adjusting to a desired size. This may be useful in situations where inspectors desire to utilize the same waveguide to test wooden specimen of vastly different lengths/widths.

In alternative examples (not shown), a pneumatic system or device may be utilized to apply pressure (e.g., air pressure) to the impact surface 412 to drive the waveguide into the wooden specimen. In some alternative examples where a pneumatic device may be determined to be ideal for securing a waveguide into a wooden specimen, it is to be understood that the impact surface 412 of the waveguide may be altered to comprise a pneumatic interface component that fosters a connection with a pneumatic device to connect with the impact surface to provide the pressure for driving the waveguide into the wood. In one example, the waveguide may be threaded (e.g., formulated as a self-tapping screw to aid insertion of the waveguide into the wooden specimen via pneumatic device). Engineering design that may be utilized to fabricate the impact surface for interfacing with a pneumatic system are known to one skilled in the field of art.

Figure 5:
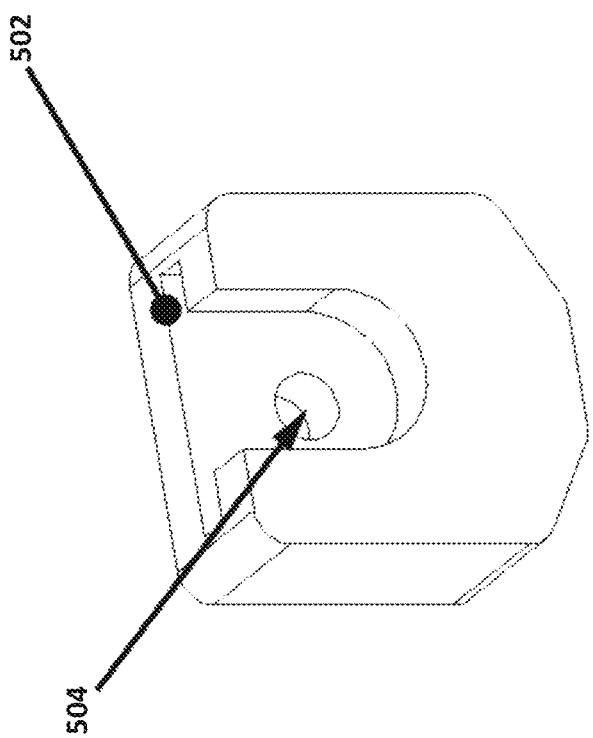
FIG. 5 illustrates a side view providing non-limiting examples of an exemplary interfacing component, with which aspects of the present disclosure may be practiced.

FIG. 5 illustrates a side view 500 providing non-limiting examples of an exemplary interfacing component, with which aspects of the present disclosure may be practiced. As described in the foregoing description, an exemplary interfacing component is utilized to secure a device (e.g., an ultrasonic transducer) to the waveguide thereby creating a handsfree configuration for NDE of wooden specimen. In non-limiting examples, interfacing component may comprise but is not limited to components such as: a base portion (illustrated as the entirety of the interfacing component in side view 500); a holding slot 502, fabricated within the base portion, and an aperture 504 at an end portion of the base portion. In alternative examples, an end portion of the base portion may comprise, instead of an aperture 504, a clamping component to secure devices to the waveguide, for example, in instances where a device such as an ultrasonic transducer is unthreaded. An exemplary base portion of the interfacing component may be formulated out of any solid and rigid material. Non-limiting examples of such materials comprise but are not limited to: plastics, metals, alloys, polycarbonates, ceramics and glass, among other examples. The holding slot 502 is configured to enable the interfacing component to attach to the waveguide. The holding slot 502 is usable to secure the interfacing component directly to the waveguide (e.g., the interfacing component is mounted on the waveguide). For instance, the holding slot 504 is fabricated as a vertical gap within a top portion of the base portion that enables the interfacing component to be slid onto the waveguide or interface with the waveguide via the holding slot 504. The holding slot 502 is configured to fit the dimensions of the waveguide. The aperture 504 is positioned at an end portion of the base portion (e.g., on a specific side of the base portion) to enable an ultrasonic device to connect to one side of the interfacing component, where the opposite side houses the waveguide (e.g., in the holding slot 504). The aperture 504, or alternatively a clamping component, is configured to enable the transducer horn of an ultrasonic transducer to contact the contact well of the waveguide when the interfacing component is attached to the waveguide and the ultrasonic transducer.

Figure 6:
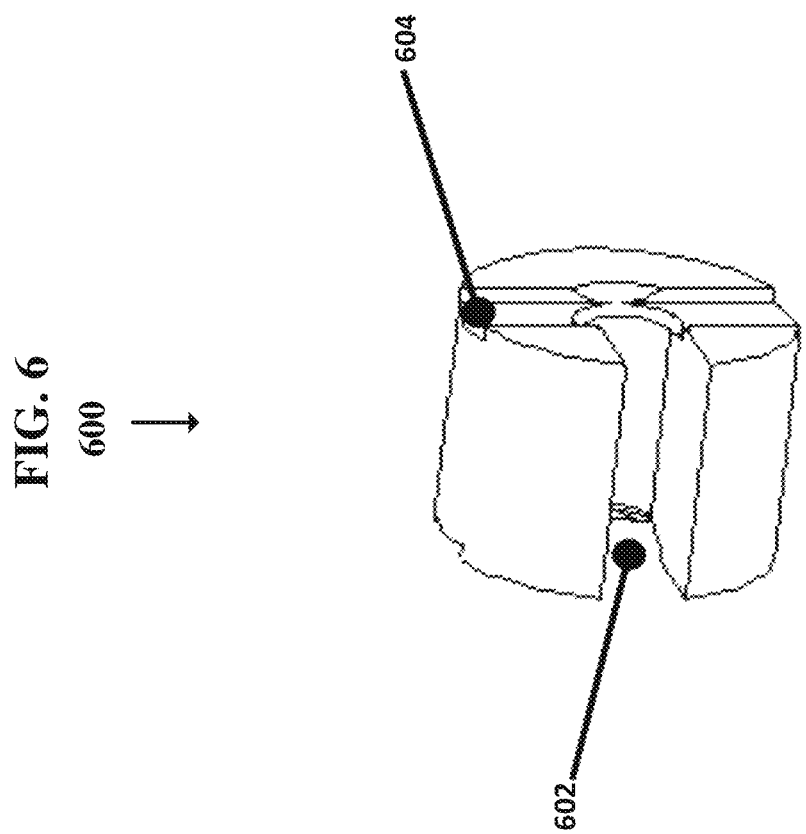
FIG. 6 illustrates a side view providing non-limiting examples of an exemplary extraction component, with which aspects of the present disclosure may be practiced.

FIG. 6 illustrates a side view 600 providing non-limiting examples of an exemplary extraction component, with which aspects of the present disclosure may be practiced. As described in the foregoing, an exemplary extraction component is configured for safe removal of the waveguide from the wooden structure to mitigate damage to the waveguide upon extraction. In non-limiting examples, the extraction component may comprise but is not limited to components such as: a base portion (illustrated as the entirety of the extraction component in side view 600); a channel 602 fabricated in the base portion; and one or more extraction slots 604, fabricated on one or more end portions of the base portion. An exemplary base portion of the extraction component may be formulated out of any solid and rigid material. Non-limiting examples of such materials comprise but are not limited to: plastics, metals, alloys, polycarbonates, ceramics and glass, among other examples. The channel 602 is usable to secure the extraction component directly to the waveguide (e.g., the extraction component is mounted on the waveguide). The channel 602 is configured to fit the dimensions of the waveguide. The one or more extraction slots 604 are usable to enable one or more tools to be inserted into the one or more extraction slots 604 for controlled removal of the waveguide from the wooden structure. For example, a tool such as a screwdriver or the like may be inserted into the one or more extraction slots 604, where pressure may be applied to the one or more extraction slots 604 via the tool in a manner where the waveguide is properly stabilized and secured through the channel 602. This configuration minimizes damage to the waveguide that may typically occur during extraction by hand or via a prying tool or the like.

Figure 7:
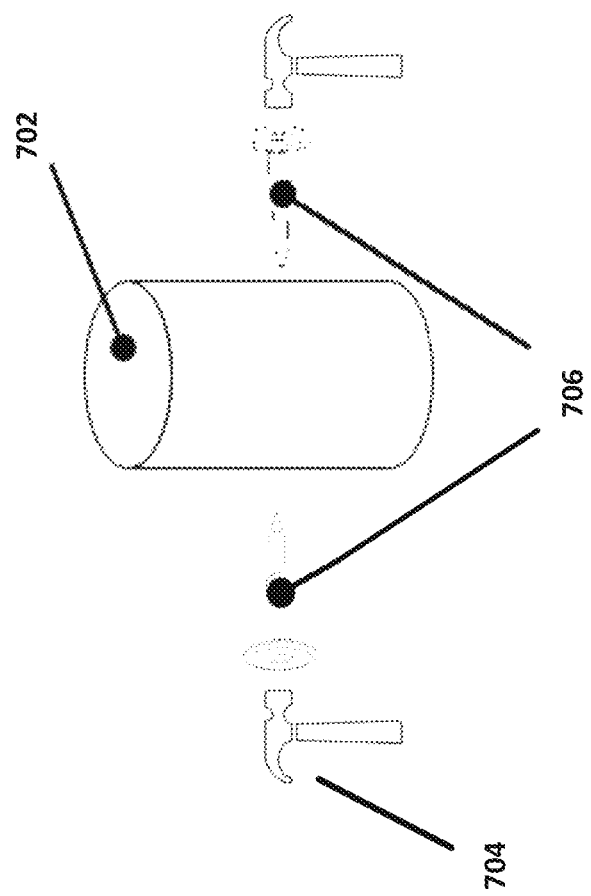
FIG. 7 illustrates a side view providing a non-limiting example of insertion of a waveguide into a wooden specimen, with which aspects of the present disclosure may be practiced.

FIG. 7 illustrates a side view 700 providing a non-limiting example of insertion of a waveguide into a wooden specimen, with which aspects of the present disclosure may be practiced. Exemplary waveguides 706 may be driven into a wooden specimen 702 (e.g., a wooden cylinder or wooden utility pole) via a tool 704 (e.g., a hammer). Side view 700 illustrates exemplary waveguide as shown in FIG. 4, where the waveguides are fabricated to comprise a visual depth indicator (e.g., visual depth indicator 404). The end portion of the upper body portion 406 of the waveguide is what is driven into the wooden specimen 702, where an inspector may contact the impact surface 412 until the upper body portion 406 is driven into the wooden specimen 702 up to a point of the visual depth indicator 404.

Figure 8:
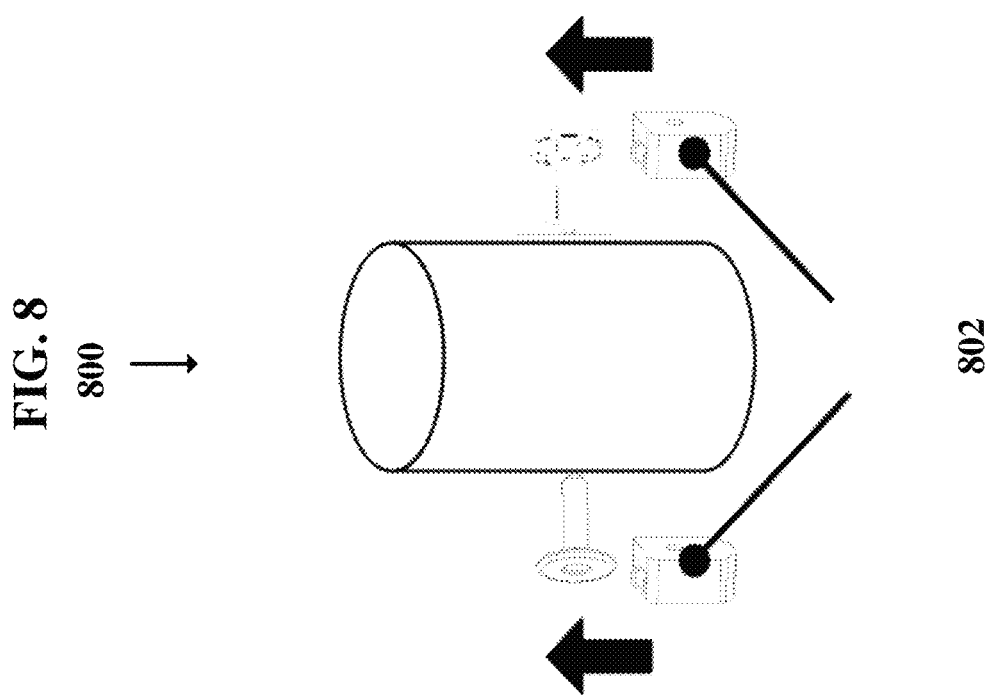
FIG. 8 illustrates a side view illustrating a non-limiting example of an interaction between a waveguide and a coupling interface component, with which aspects of the present disclosure may be practiced.

FIG. 8 illustrates a side view 800 illustrating a non-limiting example of an interaction between a waveguide and a coupling interface component, with which aspects of the present disclosure may be practiced. An exemplary coupling interface component 802 may be an interface component as described in the foregoing description, where the coupling interface component 802 may be mounted on a waveguide that is embedded in wooden specimen. As described in the foregoing description, including the description of FIG. 5, A holding slot of the coupling interface component 802 (e.g., holding slot 502 as described in FIG. 5) is configured to enable the coupling interface component 802 to attach to the waveguide. The holding slot is usable to secure the coupling interface component 802 directly to the waveguide (e.g., the interfacing component is mounted on the waveguide). For instance, as described in the foregoing, the holding slot is a vertical gap within a top portion of the base portion that enables the coupling interface component 802 to be slid onto the waveguide or interface with the waveguide via the holding slot. The holding slot is configured to allow an impact surface of the waveguide to be completely placed in the holding slot. Furthermore, the coupling interface component 802 may comprise a connection means to secure an ultrasonic device to the waveguide via the mounted coupling interface component 802. A transducer aperture or transducer horn may be positioned at an end portion of the base portion (e.g., on a specific side of the base portion) to enable an ultrasonic device to connect to one side of the coupling interface component 802 where the opposite side houses the waveguide (e.g., in the holding slot). The aperture, or alternatively a clamping component, is configured to enable the tip of the transducer horn of an ultrasonic transducer to contact the contact well of the waveguide when the coupling interface component 802 is attached to the waveguide and the ultrasonic transducer.

Figure 9:
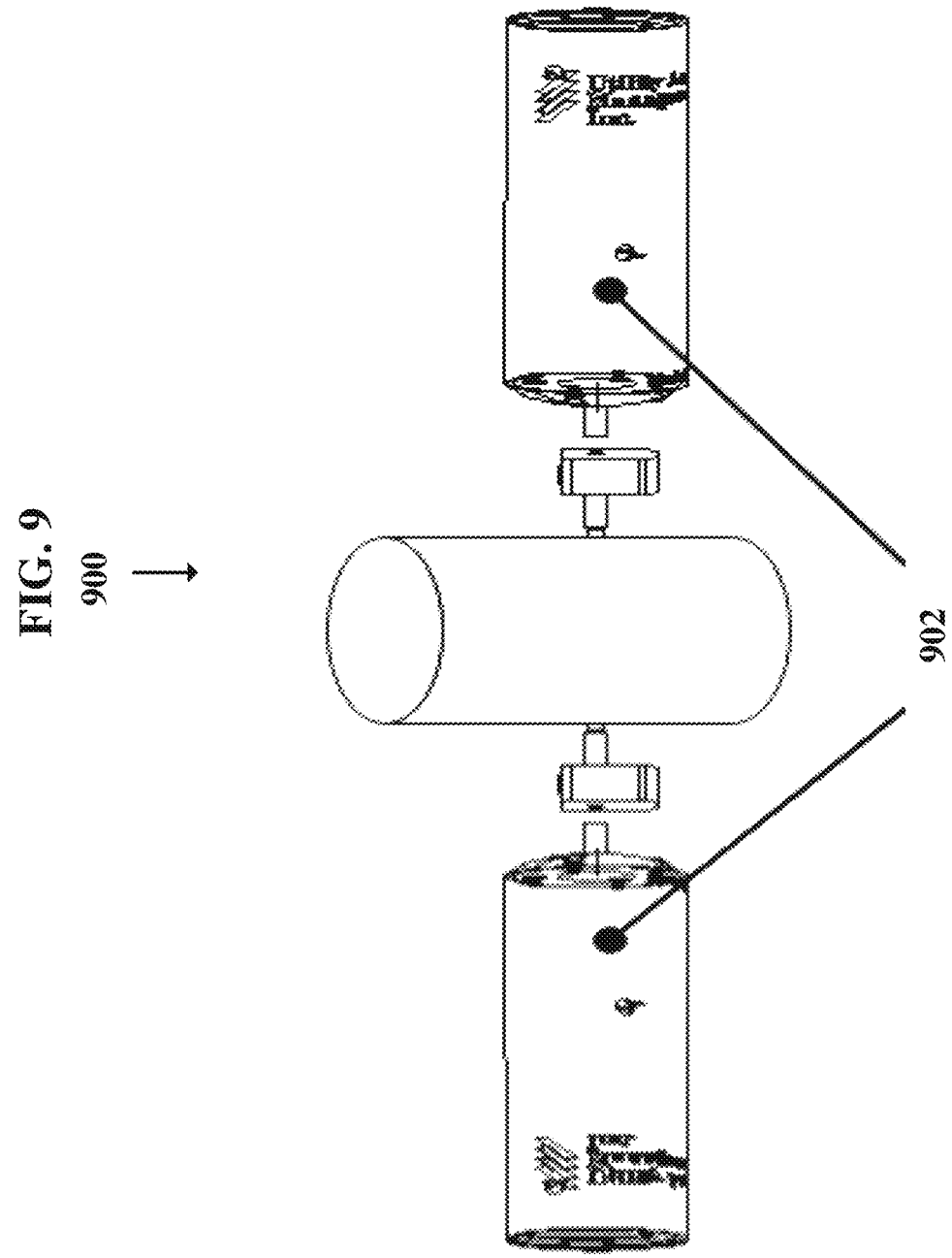
FIG. 9 illustrates a side view illustrating a non-limiting example of an interaction between a non-destructive evaluation (NDE) device, a coupling interface component and a waveguide, with which aspects of the present disclosure may be practiced.

FIG. 9 illustrates a side view 900 illustrating a non-limiting example of an interaction between an NDE device, a coupling interface component and a waveguide, with which aspects of the present disclosure may be practiced. Some previous examples describe connection of an ultrasonic device directly to a waveguide. In further examples, an NDE device may be tailored for the specific purpose of ultrasonic testing of a wooden specimen via NDE. Side view 900 illustrates an exemplary NDE device 902 being mounted to an inserted waveguide, which is inserted into a wooden specimen via an interface component/coupling interface component.

An exemplary NDE device 902 may comprise: a transducer assembly that comprises an ultrasonic transducer; an electronic processing assembly that comprises a printed circuit assembly and a processing unit; and a casing assembly, that houses the transducer assembly and the electronic processing assembly. The casing assembly is configured, at an end portion, to attach to the waveguide, via a mating portion of the waveguide, for NDE of a wooden specimen such as a wooden cylinder or a wooden utility pole. The NDE device 902 may be configured to receive, from the ultrasonic transducer, ultrasonic signal data and transmit, to a computing device, the ultrasonic signal data via a data transmission component of its processing unit. In additional examples described herein, multiple NDE devices 902 may be attached to a wooden specimen, via multiple waveguides, to enable more comprehensive testing of structural integrity of a wooden specimen. Side view 900 illustrates an example where NDE devices 902 are inserted on opposing sides of a wooden specimen. For example, a first NDE device may be configured as a transmitting device, for transmitting of ultrasonic signal data, and a second NDE device may be configured as a receiving device to receive transmitted ultrasonic signal data. Data from both devices may be propagated to a computing device that may be configured to analyze the ultrasonic signal data.

Figure 10:
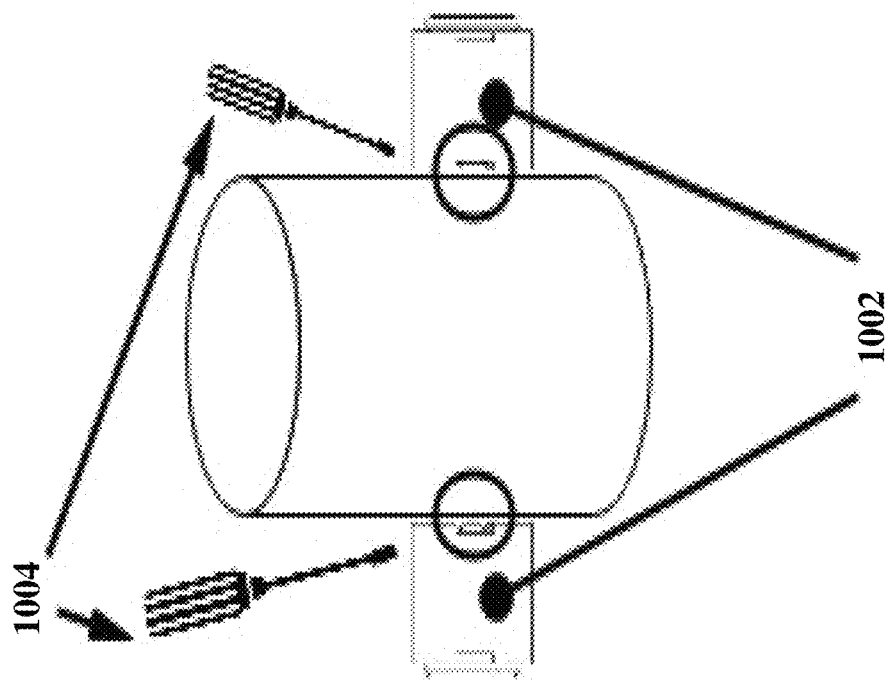
FIG. 10 illustrates a side view illustrating a non-limiting example of an interaction between a waveguide and an extraction component, with which aspects of the present disclosure may be practiced.

FIG. 10 illustrates a side view 1000 illustrating a non-limiting example of an interaction between a waveguide and an extraction component, with which aspects of the present disclosure may be practiced. An exemplary extraction component 1002 and interactions therewith have been previously described in the foregoing description including the description of FIG. 6. Side view 1000 illustrates the process for using one or more tools 1004 to engage the extraction component 1002 (or multiple extraction components as shown in side view 1000) for safe removal of waveguides from a wooden specimen. For example, the one or more tools 1004 may be inserted into one or more extraction slots (circled in side view 1000) of an extraction component 1002. When pressure is applied via the one or more tools 1004, the extraction component 1002 secures the waveguide while pressure is applied thereto, and the waveguide is extracted from the wooden specimen. As referenced in the foregoing description, an extraction component may not be necessary to remove an exemplary waveguide from a wooden specimen as the waveguide can be carefully removed by hand.

Figure 11:
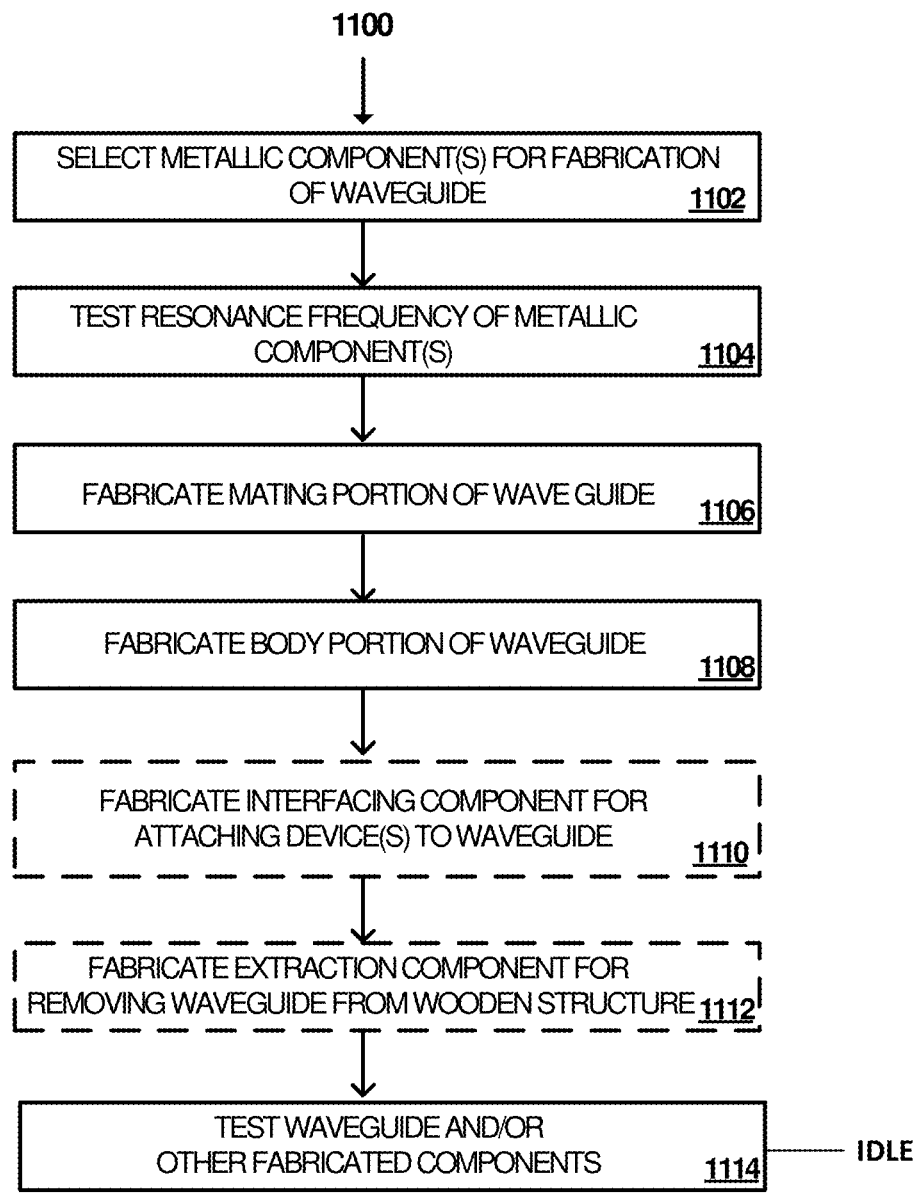
FIG. 11 illustrates an exemplary method of manufacturing a waveguide and other associated components such as an interfacing component and an extraction component, with which aspects of the present disclosure may be practiced.

FIG. 11 illustrates an exemplary method 1100 of manufacturing a waveguide and other associated components such as an interfacing component and an extraction component, with which aspects of the present disclosure may be practiced. While, for purposes of simplicity of explanation, method 1100 may be in the form of a functional diagram, operational scenario or sequence, or flow diagram, and may be described as a series of acts, it is to be understood and appreciated that the methods are not limited by the order of acts, as some acts may, in accordance therewith, occur in a different order and/or concurrently with other acts from that shown and described herein.

Method 1100 begins at processing operation 1102, where one or more metallic components are selected for fabrication of an exemplary waveguide. Examples of metallic components have been provided in the foregoing description. In some examples, an exemplary metal used to manufacture a waveguide may match the metal type of an ultrasonic device (e.g., that of a transducer horn of an ultrasonic transducer) to optimize signal transmission therethrough. The goal of testing (processing operation 1102) is to identify materials that can achieve a desires resonance frequency for optimizing ultrasonic waves for NDE of a wooden specimen. The waveguide is fabricated to generate a resonance frequency that matches a resonance frequency of an ultrasonic wave for non-destructive evaluation (NDE) of a wooden specimen being tested such as a wooden utility pole. Also, an exemplary waveguide may be fabricated out of a material that matches a transducer horn to reduce impedance mismatch, which may comprise a material that matches that of a transducer horn.

Flow of method 1100 may proceed to processing operation 1104, where resonance frequency of the selected metallic component(s) may be tested. In some instances, processing operation 1104 may comprise aggregating data on specific types of metals and/or specific types of woods with respect to resonance frequencies. This type of data may optimize selection of a material for an exemplary waveguide. For example, a database may be maintained correlating aggregated data with resonance frequencies that can be referenced when a waveguide is to be fabricated for specific implementation (e.g., utility pole, construction site, saw mill) and/or a specific type of wood specimen (e.g., pine, oak, cedar). Testing (processing operation 1104) is an optional step that may not need to be repeated in all manufacturing scenarios.

Once one or more metallic components are selected and tested, flow of method 1100 may proceed to fabricating the waveguide. As referenced in the foregoing description, an exemplary waveguide is fabricated at a predetermined resonance frequency that matches a resonance frequency of an optimal ultrasonic wave for non-destructive evaluation (NDE) of a wooden specimen. The waveguide may be fabricated from single piece of metal or a plurality of different pieces of metal that are forged together (e.g., soldered). As a non-limiting example, an exemplary waveguide is fabricated so the resonance frequency of said waveguide resonates at 50 kHz. However, it is to be understood that the waveguide can be fabricated to resonate at any desired frequency (or range of frequencies) without departing from the spirit of the present disclosure. Fabricating of the waveguide may comprise machining specific portions of the waveguide as described in the foregoing description. Processing for machining mechanical components of a waveguide is known to one skilled in the field of art.

At processing operation 1106, a mating portion of the waveguide is fabricated. Examples of a mating portion have been described in the foregoing description. Processing operation 1106 may comprise fabricating, out of metal, components that may comprise but are not limited to: an impact surface, a contact well and an amplifying cone, among other examples.

Processing of method 1100 may proceed to processing operation 1108, where a body portion of the waveguide is fabricated. Processing operation 1108 may comprise fabricating, out of metal, components that may comprise but are not limited to: a radiating component that comprises an upper body portion, that is designed to make contact with a wooden specimen (e.g., drivable to penetrate into the wooden specimen or contact without penetration), and a lower body portion that is attached to and extends outwardly from the upper body portion and is attached to the mating portion; and an end portion that may contact a wooden specimen, among other examples.

In some alternative examples of method 1100, additional components may also be manufactured including but not limited to: an interfacing component (e.g., coupling interface component) and an extraction component. In examples where an interfacing component is to be manufactured, flow of method 1100 proceeds to processing operation 1110, where the interfacing component is fabricated. Processing operation 1110 may comprise fabricating components that may comprise but are not limited to: a base portion; a holding slot, fabricated within the base portion, and an aperture at an end portion of the base portion. In alternative examples, an end portion of the base portion may comprise, instead of an aperture, a clamping component to secure devices to the waveguide, for example, in instances where a device such as an ultrasonic transducer is unthreaded. An exemplary base portion of the interfacing component may be formulated out of any solid and rigid material. Non-limiting examples of such materials comprise but are not limited to: plastics, metals, alloys, polycarbonates, ceramics and glass, among other examples. Fabricating of an exemplary interfacing component may comprise machining specific portions of the interfacing component as described in the foregoing description. Processing for machining mechanical components of the interfacing component is known to one skilled in the field of art. In at least one example, the interfacing component is generated using a 3D printer.

In examples where an extraction component is to be manufactured, flow of method 1100 proceeds to processing operation 1112, where the extraction component is fabricated. Processing operation 1112 may comprise fabricating components that may comprise but are not limited to: a base portion; a channel fabricated in the base portion; and one or more extraction slots 604, fabricated on one or more end portions of the base portion. An exemplary base portion of the interfacing component may be formulated out of any solid and rigid material. Non-limiting examples of such materials comprise but are not limited to: plastics, metals, alloys, polycarbonates, ceramics and glass, among other examples. Fabricating of an exemplary extraction component may comprise machining specific portions of the extraction component as described in the foregoing description. Processing for machining the extraction component is known to one skilled in the field of art. In at least one example, the extraction component is generated using a 3D printer.

Once an exemplary waveguide is fabricated and/or other associated components are fabricated, flow of method 1100 may proceed to processing operation 1114. At processing operation 1114, the waveguide, among other fabricated components, may be tested to ensure the waveguide is properly constructed and operating at the optical resonance frequency for NDE of wooden structures. For instance, processing operation 1114 comprises checking a resonance frequency of a fabricated waveguide. Processing for evaluating a resonance frequency of a metal object is known to one skilled in the field of art. In one example, the waveguide may be tested in the field using one or more NDE devices and computing devices. In examples where an interfacing component and/or an extraction component are fabricated, quality checks may also be performed on said components. Processing operation 1114 may further comprise modifying scientific parameters (e.g., voltage) to test operation of the waveguide under different environmental conditions.

Figure 12:
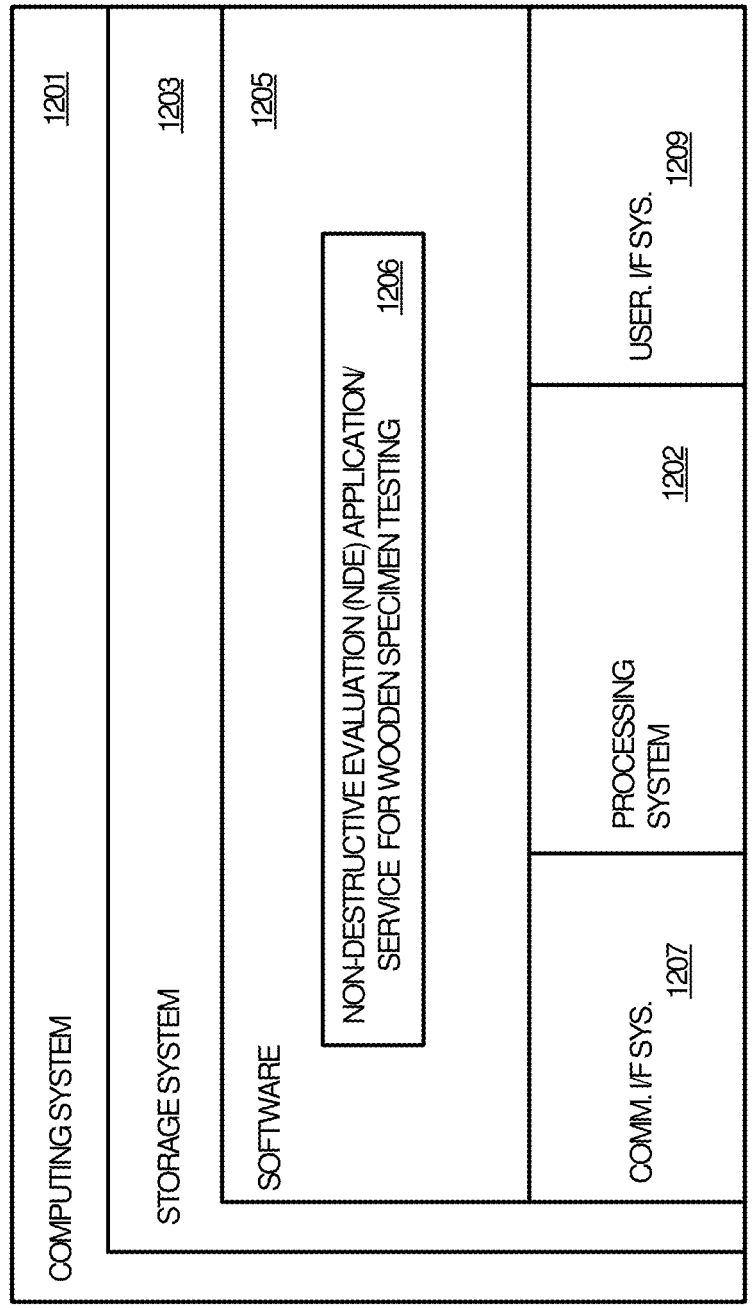
FIG. 12 illustrates a computing device for NDE of a wooden specimen, with which aspects of the present disclosure may be practiced.

FIG. 12 illustrates a computing system 1201 suitable for implementing processing operations described herein related to a computing device for NDE of a wooden specimen, with which aspects of the present disclosure may be practiced. For example, computing system 1201 may be configured to execute an NDE application/service that is configured to control NDE of a wooden specimen in which an exemplary waveguide and other components may be attached. The NDE application/service may be configured to execute processing operations that may manage a waveguide component including but not limited to processing operations for: testing a connection between an NDE device and a waveguide; testing a resonance frequency of a waveguide; tuning/re-tuning a waveguide for a specific environment; and controlling transmission of ultrasonic signal data through the waveguide, among other examples. Computing system 1201 may be implemented as a single apparatus, system, or device or may be implemented in a distributed manner as multiple apparatuses, systems, or devices. For example, computing system 1201 may comprise one or more computing devices that execute processing for applications and/or services over a distributed network to enable execution of processing operations described herein over one or more services. Computing system 1201 comprises, but is not limited to, processing system 1202, storage system 1203, software 1205, communication interface system 1207, and user interface system 1209. Processing system 1202 is operatively coupled with storage system 1203, communication interface system 1207, and user interface system 1209. Non-limiting examples of computer system 1201 comprise but are not limited to: smart phones, laptops, tablets, PDAs, desktop computers, servers, smart computing devices including television devices and wearable computing devices, e-reader devices, and conferencing systems, among other non-limiting examples. Other types of processing devices may be utilized as computer system 1201 without departing from the spirit of the present disclosure.

Processing system 1202 loads and executes software 1205 from storage system 1203. Software 1205 includes one or more software components 1206 that execute an NDE application/service for utility pole testing. In some examples, computing system 1201 may be a device that a user utilizes to interface a waveguide and/or NDE device via the NDE application/service for wooden specimen testing 1206. For example, computing device 1201, through execution of the NDE application/service for wooden specimen testing 1206, interfaces with a waveguide (via an NDE device) to make sure the waveguide is configured properly for NDE of a wooden specimen such as a wooden structure, as described in the foregoing description. The computing device 1201 may interface with an NDE device, that is connected to a waveguide, via wired connection or wireless connection including any of data transmission protocols described herein as well as other known methods of data transmission as known to one skilled in the field of art. When executed by processing system 1202, software 1205 directs processing system 1202 to operate as described herein for at least the various processes, operational scenarios, and sequences discussed in the foregoing implementations. Computing system 1201 may optionally include additional devices, features, or functionality not discussed for purposes of brevity.

Computing system 1201 may further be utilized to execute control operation of NDE devices and waveguides, for example, where NDE devices, that are attached to a utility pole via a waveguide, may be configurable to change between described modes of operation either by direct commands, transmitted from computing system 1201 or via a conclusion of programmed activity (e.g., an NDE enters a standby mode when programmed processing is completed and/or NDE device disconnected/removed). Examples of modes of operation of an NDE comprise but are not limited to: a standby mode; a transmitting mode; a receiving mode; and a hybrid transmitting/receiving mode, among other examples. In instances where a computing system 1201 is transmitting commands to set an NDE device in one of the above-identified modes, commands may be transmitted to a processing unit of an NDE device that is configured to receive such commands via a data transmission component of the NDE device. As such, a computing device 1201 may be configured to implement a data transmission component that works with a same data transmission protocol that an NDE is configured to receive data through.

Referring still to FIG. 12, processing system 1202 may comprise processor, a micro-processor and other circuitry that retrieves and executes software 1205 from storage system 1203. Processing system 1202 may be implemented within a single processing device but may also be distributed across multiple processing devices or sub-systems that cooperate in executing program instructions. Examples of processing system 1202 include general purpose central processing units, microprocessors, graphical processing units, application specific processors, sound cards, speakers and logic devices, as well as any other type of processing devices, combinations, or variations thereof.

Storage system 1203 may comprise any computer readable storage media readable by processing system 1202 and capable of storing software 1205. Storage system 1203 may include volatile and nonvolatile, removable and non-removable media implemented in any method or technology for storage of information, such as computer readable instructions, data structures, program modules, cache memory or other data. Examples of storage media include random access memory, read only memory, magnetic disks, optical disks, flash memory, virtual memory and non-virtual memory, magnetic cassettes, magnetic tape, magnetic disk storage or other magnetic storage devices, or other suitable storage media, except for propagated signals. In no case is the computer readable storage media a propagated signal.

In addition to computer readable storage media, in some implementations storage system 1203 may also include computer readable communication media over which at least some of software 1205 may be communicated internally or externally. Storage system 1203 may be implemented as a single storage device but may also be implemented across multiple storage devices or sub-systems co-located or distributed relative to each other. Storage system 1203 may comprise additional elements, such as a controller, capable of communicating with processing system 1202 or possibly other systems. In some examples, storage system 1203 is a distributed network storage/web storage, where computing device 1201 is configured to connect to the distributed network storage/web storage via a network connection.

Software 1205 may be implemented in program instructions and among other functions may, when executed by processing system 1202, direct processing system 1202 to operate as described with respect to the various operational scenarios, sequences, and processes illustrated herein. For example, software 1205 may include program instructions for an NDE application/service for wooden structure testing 1206, as described in the foregoing description.

In particular, the program instructions may include various components or modules that cooperate or otherwise interact to carry out the various processes and operational scenarios described herein. The various components or modules may be embodied in compiled or interpreted instructions, or in some other variation or combination of instructions. The various components or modules may be executed in a synchronous or asynchronous manner, serially or in parallel, in a single threaded environment or multi-threaded, or in accordance with any other suitable execution paradigm, variation, or combination thereof. Software 1205 may include additional processes, programs, or components, such as operating system software, virtual machine software, or other application software. Software 1205 may also comprise firmware or some other form of machine-readable processing instructions executable by processing system 1202.

In general, software 1205 may, when loaded into processing system 1202 and executed, transform a suitable apparatus, system, or device (of which computing system 1201 is representative) overall from a general-purpose computing system into a special-purpose computing system customized to process data and respond to queries. Indeed, encoding software 1205 on storage system 1203 may transform the physical structure of storage system 1203. The specific transformation of the physical structure may depend on various factors in different implementations of this description. Examples of such factors may include, but are not limited to, the technology used to implement the storage media of storage system 1203 and whether the computer-storage media are characterized as primary or secondary storage, as well as other factors.

For example, if the computer readable storage media are implemented as semiconductor-based memory, software 1205 may transform the physical state of the semiconductor memory when the program instructions are encoded therein, such as by transforming the state of transistors, capacitors, or other discrete circuit elements constituting the semiconductor memory. A similar transformation may occur with respect to magnetic or optical media. Other transformations of physical media are possible without departing from the scope of the present description, with the foregoing examples provided only to facilitate the present discussion.

Communication interface system 1207 may include communication connections and devices that allow for communication with other computing systems (not shown) over communication networks (not shown). Communication interface system 1207 may also be utilized to cover interfacing between processing components described herein. Examples of connections and devices that together allow for inter-system communication may include network interface cards or devices, wired and/or wireless modules, antennas, power amplifiers, RF circuitry, transceivers, and other communication circuitry. The connections and devices may communicate over communication media to exchange communications with other computing systems or networks of systems, such as metal, glass, air, or any other suitable communication media. The aforementioned media, connections, and devices are well known and need not be discussed at length here.

User interface system 1209 is optional and may include a keyboard, a mouse, a voice input device, a touch input device for receiving a touch gesture from a user, a motion input device for detecting non-touch gestures and other motions by a user, and other comparable input devices and associated processing elements capable of receiving user input from a user. Output devices such as a display, speakers, haptic devices, and other types of output devices may also be included in user interface system 1209. In some cases, the input and output devices may be combined in a single device, such as a display capable of displaying images and receiving touch gestures. The aforementioned user input and output devices are well known in the art and need not be discussed at length here.

User interface system 1209 may also include associated user interface software executable by processing system 1202 in support of the various user input and output devices discussed above. Separately or in conjunction with each other and other hardware and software elements, the user interface software and user interface devices may support a graphical user interface, a natural user interface, or any other type of user interface, for example, that enables front-end processing of exemplary application/services described herein (including an NDE application/service for wooden specimen testing 1206). User interface system 1209 comprises a graphical user interface that is configured to enable users to transmit/receive commands for a state of an NDE device and to toggle a state of an NDE device (e.g., change a mode of an NDE device for specific task related to wooden specimen testing). Additionally, the graphical user interface may be configured to display user interface elements related to the testing and operation of an exemplary waveguide. For example, a connection between a waveguide and a transducer horn, including contact therebetween, may be represented through the graphical user interface. In further examples, the graphical user interface may be configured to display user interface elements related to a state of the waveguide as well as enable executions of commands and receipt of results for testing and/or tuning of exemplary waveguides. A graphical user interface of user interface system 1209 may further be configured to display graphical user interface elements (e.g., data fields, menus, graphs, charts, data correlation representations and identifiers, etc.) that are representations generated from processing ultrasonic signal data received from one or more NDE devices. For example, processing of received ultrasonic signal data, received from one or more NDE devices, may be utilized to provide explicit statistical data regarding a condition of a wooden specimen as well as classifications of a state of wooden specimen that reflect algorithmic analysis of received ultrasonic signal data (e.g., that the wooden specimen is: tagged for replacement, flagged for re-testing at specified future time period; in good condition). Such example interpretations are non-limiting examples of the type of evaluation that can be made from received ultrasonic signal data and which may be provided as graphical user interface elements in a graphical user interface of an NDE application/service for wooden structure testing 1206.

Communication between computing system 1201 and other computing systems (not shown), may occur over a communication network or networks and in accordance with various communication protocols, combinations of protocols, or variations thereof. Examples include intranets, internets, the Internet, local area networks, wide area networks, wireless networks, wired networks, virtual networks, software defined networks, data center buses, computing backplanes, or any other type of network, combination of network, or variation thereof. The aforementioned communication networks and protocols are well known and need not be discussed at length here. However, some communication protocols that may be used include, but are not limited to, the Internet protocol (IP, IPv4, IPv6, etc.), the transfer control protocol (TCP), and the user datagram protocol (UDP), Bluetooth, infrared, RF, cellular networks, satellite networks, global positioning systems, as well as any other suitable communication protocol, variation, or combination thereof.

In any of the aforementioned examples in which data, content, or any other type of information is exchanged, the exchange of information may occur in accordance with any of a variety of protocols, including FTP (file transfer protocol), HTTP (hypertext transfer protocol), REST (representational state transfer), WebSocket, DOM (Document Object Model), HTML (hypertext markup language), CSS (cascading style sheets), HTML5, XML (extensible markup language), JavaScript, JSON (JavaScript Object Notation), and AJAX (Asynchronous JavaScript and XML), as well as any other suitable protocol, variation, or combination thereof.

Figure 13:
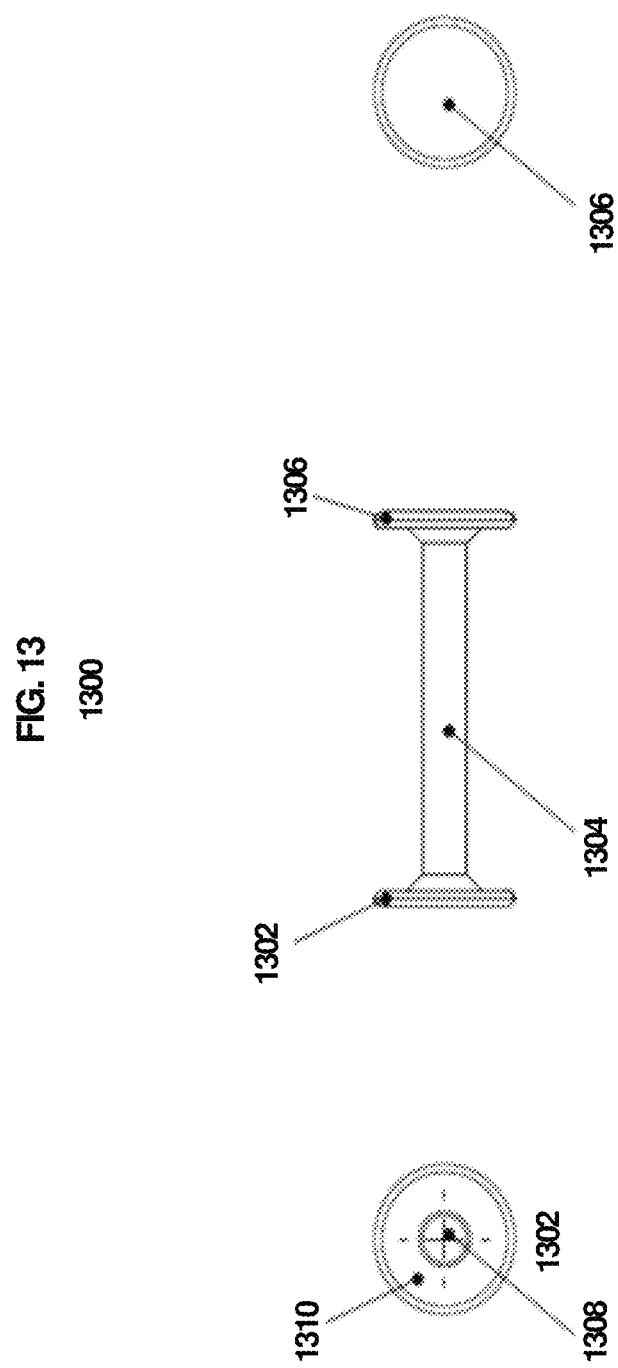
FIG. 13 illustrates a side view providing non-limiting examples of a waveguide that optimized to conduct NDE of a wooden specimen without requiring the waveguide to be driven into the wooden specimen, with which aspects of the present disclosure may be practiced.

FIG. 13 illustrates a side view 1300 providing non-limiting examples of a waveguide that optimized to conduct NDE of a wooden specimen without requiring the waveguide to be driven into the wooden specimen, with which aspects of the present disclosure may be practiced. Side view 300 illustrates components of the modified waveguide design, where an upper body portion of an exemplary waveguide is fabricated to enable contact with the wooden specimen such that a distal end of the upper body portion may abut a surface of a wooden specimen. This helps minimize the risk of causing additional damage/decay to a wooden specimen during NDE which may result in other technical instances that require penetrating the surface of the wooden specimen. In order to enable the waveguide to contact a surface of a wooden specimen, a user may apply an appropriate amount of pressure (e.g., 5 or more pounds of pressure) to an assembled unit (NDE device that is attached to the waveguide via an interfacing component) to enable the waveguide thereof to contact the wooden specimen. For instance, a user may hold/stabilize an assembled unit such that the upper body portion (radiating component) contacts a surface of the wooden specimen. The NDE device may then be activated to conduct NDE of the wooden specimen, capturing acoustic signal data that may be stored on an NDE device and subsequently transmitted for subsequent analysis to evaluate a state of the wooden specimen.

In alternative examples, the modified waveguide design enables a handsfree approach to establish contact between a waveguide and a wooden specimen without requiring penetration through a surface of the wooden specimen. For instance, an adhesive may be applied to the waveguide and/or a specific location on specimen to which the waveguide attaches, thereby establishing secure contact between the waveguide and the specimen for NDE. Any type of adhesive may be applied as known to one skilled in the field of art. Non-limiting examples of such adhesives comprise but are not limited to: glues, resins, epoxies, sprays, pressure adhesives, conductive adhesives and tapes (e.g., double-sided tape), among other examples. In one specific example, fabrication of the waveguide may comprise application of an activatable adhesive on an upper body portion of the waveguide. In another example, an adhesive may be mixed into a couplant that is contacting the waveguide and wooden specimen, thereby fostering secure contact between the waveguide and the wooden specimen. In yet another alternative example, an apparatus may be used to stabilize an assembled unit (NDE device attached to waveguide via an interfacing component) to the surface of the specimen and thereby provide handsfree capability with more consistent pressure as compared to a user manually holding the assembled unit against a surface of the wooden specimen. Exemplary stabilizing apparatuses may secure the assembled unit to a surface of a wooden specimen through one or more of a mechanical mechanism, an electromechanical mechanism, a pneumatic mechanism or a combination thereof. Non-limiting examples of such apparatuses comprise but are not limited to clamps, brackets, and suction cups, among other examples.

In examples where an adhesive (e.g., small moderate amount proportionally) is applied, a proper amount of force can be applied to disengage the NDE device/waveguide from the wooden specimen. As an alternative method of removal when an adhesive is utilized, an additional substance may be applied to dissolve the adhesive to assist with disengaging the NDE device/waveguide from the wooden specimen. Examples of substances that could be used to break/weaken an adhesive bond are known to one skilled in the field of art. In some further examples, a tool (e.g., a scraper, screwdriver) may further be utilized to assist with removal of the waveguide from the surface of the wooden specimen.

As shown in the center illustration of side view 1300, the exemplary waveguide comprises a mating portion 1302, a lower body portion 1304 and an upper body portion 1306. The mating portion 1302, a lower body portion 1304 and an upper body portion 1306, and/or components thereof, may be fabricated in any shape without departing from the spirit of the present disclosure, including but not limited to shapes such as: circular, square, hexagonal, triangular, rectangular or any other cross-sectional geometries. In some instances, the upper body portion 1306 may differ in shape from other components such as the lower body portion 1304 as show in the illustration in side view 1300. The mating portion 1302 may be a coupling flange configured to enable interfacing between the waveguide and a transducer horn of an ultrasonic transducer as described in the foregoing description. In some examples, the mating portion 1302 may comprise a contact well 1308 and/or an impact surface 1310, where the contact well 1308 is fabricated to be indented within the impact surface 1310 to help protect the contact interface between the transducer horn and the waveguide from any external damage. A diameter of the contact well 1308 may vary during fabrication to accommodate transducer horns with different diameters. In at least one example, the mating portion 1302 may be interchangeable where a user can change out the mating portion 1302 when working out in the field with transducer horns have different diameters.

In some alternative examples where a specific model of the waveguide is not to be driven into a wooden specimen, a distal end of the waveguide may be fabricated with only a contact well or flat surface similar to the representation illustrated for the upper body portion 1306 of side view 1300. As such, a separate impact surface 1310 may not be required as the waveguide does not need to be driven into a wooden specimen to obtain a signal reading during NDE. In one instance, an exemplary contact well 1308 may be circular in shape to securely attach to a transducer horn of an ultrasonic transducer. However, it is to be recognized that the contact well may be fabricated in any shape to fit any type of device that is interfacing with the waveguide without departing from the spirit of the present disclosure. In alternative examples, an exemplary waveguide may be threaded to enable insertion of the waveguide into a wooden specimen without the need to use a hammer, mallet, pneumatic device. For instance, a contact well 1308 may be tapped during fabrication so that a threaded transducer horn can be directly mounted to the waveguide without the use of a mating interface.

The waveguide further comprises a body portion that extends from the mating portion 1302 to formulate a single NDE component. The body portion comprises the lower body portion 1304 and an upper body portion 1306. The lower body portion 1304 is attached to the upper body portion 1306 and the mating portion 1302 acting as an interface therebetween. The upper body portion 1306 is fabricated to extend outwardly from the lower body portion 1304. An exemplary upper body portion 1306 is a radiating component, projecting outwardly from the lower body portion 1304 where a distal end is configured to contact a surface of a specimen (e.g., a wooden specimen). In one instance, the upper body portion 1306 has a flat-faced distal end (e.g., shown in side view 1300 as being circular in shape). That is, the upper body portion 1306 comprises a flat-faced distal end that is usable to establish contact with a surface of the wood specimen. The lower body portion 1304 may be a shank portion that guides an acoustic wave (ultrasonic wave), from an attached transducer (transducer horn) via the contact well 1308, to the radiating component (upper body portion 1306) for transmission and receipt of wave signals through the wooden specimen. The entire configuration of the body of the waveguide optimizes propagation of ultrasonic waves through the contact well 1308 into the wooden specimen through the body portions of the waveguide. A flat-faced radiating component of the upper body portion 1306 may have a larger diameter than the lower body portion 1304 (e.g., shank body) to thereby increase the contact area with the wooden specimen. In turn, this fabricated configuration amplifies the transmission and reception of an ultrasonic signal for NDE.

Figure 14:
FIG. 14 illustrates a side view providing a non-limiting example of an assembled unit that comprises a waveguide attached to an NDE device via an interfacing component, with which aspects of the present disclosure may be practiced.

FIG. 14 illustrates a side view 1400 providing a non-limiting example of an assembled unit that comprises a waveguide 1402 attached to an NDE device 1406 via an interfacing component 1404, with which aspects of the present disclosure may be practiced. Each of the waveguide 1402, the interfacing component 1404 and the NDE device 1406 have been described in detail in the foregoing description. Side view 1400 provides an illustration to visualize how the assembled unit appears when the waveguide 1402 is attached to NDE device 1406 via the interfacing component 1404.

Figure 15A:
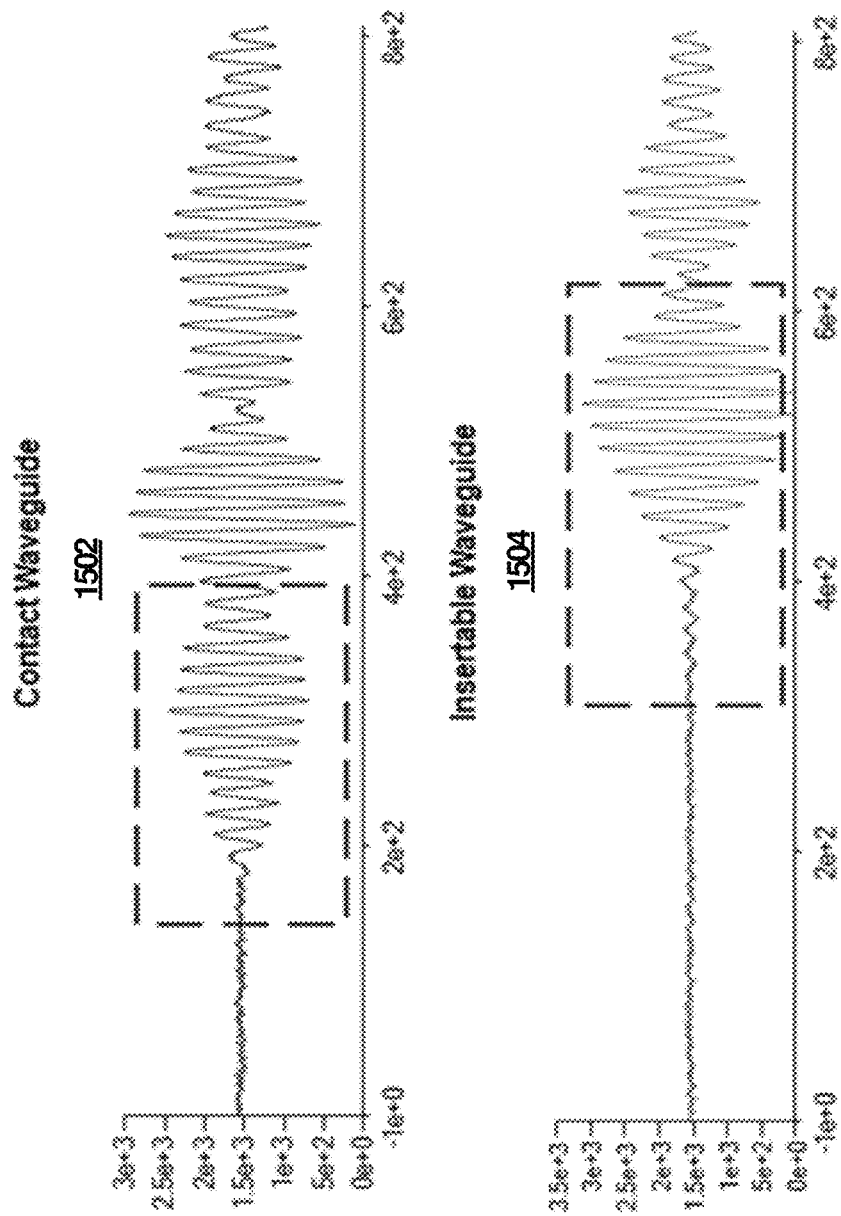

FIGS. 15A and 15B illustrate comparative graphing providing a signal comparison between exemplary waveguide designs that penetrate a specimen and exemplary waveguide designs that contacts a specimen without penetrating the specimen, with which aspects of the present disclosure may be practiced. Comparative graphing 1500 (FIG. 15A) and comparative graphing 1520 (FIG. 15B) provide results of an investigation conducted to evaluate the differences in signals obtained with the contact-based waveguides and insertable waveguides. To achieve a proper comparative evaluation, an assembled unit configured with a contact-based waveguide (does not penetrate a surface of a wooden specimen) was attached to a wooden specimen proximate to an assembled unit configured with an insertable waveguide (penetrates the wooden specimen). For example, respective assembled units were placed on the same wooden specimen (e.g., wooden utility pole) separated at 2 inches apart such that the same portion of the wooden specimen was being evaluated. In between the two assembled units, the air is used as a medium. That is due to its isotropic and homogenous property. In other words, air is an ideal medium to eliminate the variation that can erroneously introduce unwanted variations in the signals. Comparative graphing 1500 illustrates the raw data from the different waveguide configurations, where a contact waveguide graph 1502 pertains to signal data received from the contact-based waveguide configuration and insertable waveguide graph 1504 insertable waveguide pertains to signal data received from the insertable waveguide configuration. Each of the comparative graphs (1502 and 1504) show the strength of respective ultrasonic waves over a time period captured in microseconds.

The raw data show a distinct difference between the two waveguides. Prior to 200 microseconds, the signals in both graphs (1502 and 1504) exhibit ambient white noise characteristics, indicating the ambient environment of a receiving probe. When the ultrasonic signal arrives, the signal exhibit a gradual increase and decrease in the amplitude of sinusoidal oscillation forming wave packets. The initial wave packet in the contact-based waveguide configuration (shown in graph 1502) occurs at a much earlier time due to the flat-headed upper body portion (radiating interface). Since the upper body portion of the contact-based waveguide configuration has a greater radiating area compared to that of an insertable waveguide, the contact-based waveguide configuration enhances the initial arrival of wave energy. Hence, it produces a strong initial detectable wavefront. The upper body portion of the insertable waveguide configuration has a much smaller radiating aperture (pointed front end). As such, no initial wavefront is detected where only the subsequent wave energy is detected.

Comparative graphing 1520 (FIG. 15B) provide results of an investigation conducted to evaluate the differences in signals obtained with the contact-based waveguides and insertable waveguides, namely frequency domain representation. Contact waveguide graph 1522 pertains to signal data received from the contact-based waveguide configuration and insertable waveguide graph 1524 pertains to signal data received from the insertable waveguide configuration. In the frequency domain representation show in comparative graphing 1520, both waveguide configurations produce signals that peak at around 55 kHz region, indicating that both waveguides did not alter the fundamental frequency of the imposed transient load by the transducer. As such, it is clear that both are effective means of conducting NDE evaluation. While a handsfree configuration (contact-based waveguide configuration) provides some technical advantage from a usability standpoint over an insertable waveguide configuration, an insertable waveguide configuration may still be preferred in some technical instances. For instance, an insertable waveguide configuration may eliminate waveform variation due to the non-uniformities of the surface, especially wooden surfaces, when compared to that of a contact-based configuration. In essence, a more consistent response may be detected. Furthermore, an insertable waveguide configuration may also improve the ability of an ultrasonic signal to penetrate deep into the surface of a specimen due to the waveguide already being inserted therein.

FIG. 16 illustrates an exemplary method 1600 pertaining to usage of an exemplary waveguide for NDE of a specimen, with which aspects of the present disclosure may be practiced. Specifics regarding components and interactions thereof have been described in detail in the foregoing description. While, for purposes of simplicity of explanation, method 1600 may be in the form of a functional diagram, operational scenario or sequence, or flow diagram, and may be described as a series of acts, it is to be understood and appreciated that the methods are not limited by the order of acts, as some acts may, in accordance therewith, occur in a different order and/or concurrently with other acts from that shown and described herein.

Method 1600 begins at operation 1602. At operation 1602, an exemplary waveguide is connected/attached to an interfacing component. As referenced in the foregoing description, a mating portion (e.g., coupling flange) of an exemplary waveguide may be attached to the connection provided through an exemplary interfacing component to aid securing of the waveguide in an assembled unit usable for NDE of a specimen (e.g. wooden specimen).

Next, method 1600 may proceed to operation 1604. At operation 1604, an NDE device is connected with the waveguide via the interfacing component. Operation 1602 and 1604, in combination, creates an assembled unit usable for NDE of a specimen. As referenced in the foregoing description, different types of waveguides may be utilized in different technical scenarios. For instance, a contact-based waveguide (e.g., contact waveguide) may be utilized to establish contact with a specimen without penetrating through a surface of the specimen. In other examples, an insertable waveguide (e.g., embeddable waveguide) may be utilized which is designed to penetrate a surface of a specimen. In either case, the process for connecting/attaching an NDE device to a waveguide (via an interfacing component) may occur in a similar fashion. However, the order of mounting the components may differ. For instance, when working with an insertable waveguide the waveguide may be inserted into a specimen before the NDE device and/or interfacing component are attached to the waveguide. For the contact-based waveguide, the waveguide maybe mounted/attached to the NDE device and interfacing component before applying the waveguide to the surface of the specimen.

In any example, a desired location on a specimen (e.g., wooden specimen) is identified (operation 1606) regardless of the order in which the desired location is selected. In an example where a specimen is a wooden utility pole, a desired location may be selected proximate to the base of the wooden utility pole as that is the most likely site of decay due to the wooden utility pole being secured in the ground and being subject to the most weather elements, moisture, insects, etc. However, it should be recognized that any location on a wooden specimen can be selected/identified (operation 1606). In some technical examples, multiple locations are selected for NDE on a specimen.

In some alternative examples of method 1600, a couplant may be applied (operation 1608) to the desired location on the specimen and/or the upper body portion of the waveguide. A couplant reduces reflection due to the difference in the acoustic property between any two media as known to one skilled in the field of art. An exemplary couplant is a material usable to match the acoustic impedance of the specimen (e.g., medium of the wooden specimen) and the metal used to fabricate the waveguide. In the present examples, water-based couplant is a preferred type because it is water-soluble, and it will not chemically damage the specimen being inspected. However, any type of couplant can be used. Consequently, if no couplant is used, the signal strength should appear weaker but may still be detectable. As such, NDE of a wooden specimen can still be achieved without the use of couplant via the novelty described in the present disclosure.

At operation 1610, pressure is applied so that the waveguide contacts the wooden specimen. In one example, a user (e.g., an inspector) may apply pressure to the assembled unit such that the upper body portion (radiating component) of the waveguide abuts a surface of the specimen. In alternative examples, an adhesive may be applied to the waveguide and/or surface of the specimen to establish a hold securing the waveguide and/or assembled unit to the surface of the specimen. In one specific example, fabrication of the waveguide may comprise application of an activatable adhesive on an upper body portion of the waveguide. In another example, adhesive may be mixed with the couplant or incorporated within the couplant to minimize the number of steps that a user has to perform at a site where NDE is being performed. Non-limiting examples of adhesives have been described in the foregoing description. In yet another alternative example, an apparatus may be used to stabilize an assembled unit to the surface of the specimen and thereby provide handsfree capability with more consistent pressure as compared to a user manually holding the assembled unit against a surface of the wooden specimen. Exemplary stabilizing apparatuses may secure the assembled unit to a surface of a wooden specimen through one or more of a mechanical mechanism, an electromechanical mechanism, a pneumatic mechanism or a combination thereof, as described in the foregoing description.

At operation 1612, the specimen is tested using the assembled unit (e.g., NDE device, interfacing component and waveguide). Operation 1612 may comprise activating the NDE and capturing ultrasonic signal data that is transmitted through the specimen. Furthermore, operation 1612 may comprise transmitting captured signal data to a computing system/device to generate an NDE reporting indicating a status of a wooden specimen.

Finally, at operation 1614, the waveguide is removed from contact with the specimen (e.g., wooden specimen). As referenced in the foregoing description, removal of the waveguide from contact with the specimen may vary depending on the type of connection/attachment established. In technical instances where a user applies force to establish contact, the user may simply remove the assembled unit from contact with the surface of the specimen. In examples where an apparatus or device is used to secure/stabilize the assembled unit to the specimen, the apparatus may first be removed before contact with the specimen is severed. In examples where an adhesive is used to establish a handsfree attachment, appropriate force, a tool, a dissolving agent or a combination thereof may be utilized to remove the waveguide from contact with a surface of the specimen.

The functional block diagrams, operational scenarios and sequences, and flow diagrams provided in the Figures are representative of exemplary systems, environments, and methodologies for performing novel aspects of the disclosure. While, for purposes of simplicity of explanation, methods included herein may be in the form of a functional diagram, operational scenario or sequence, or flow diagram, and may be described as a series of acts, it is to be understood and appreciated that the methods are not limited by the order of acts, as some acts may, in accordance therewith, occur in a different order and/or concurrently with other acts from that shown and described herein. For example, those skilled in the art will understand and appreciate that a method could alternatively be represented as a series of interrelated states or events, such as in a state diagram. Moreover, not all acts illustrated in a methodology may be required for a novel implementation.

The descriptions and figures included herein depict specific implementations to teach those skilled in the art how to make and use the best option. For the purpose of teaching inventive principles, some conventional aspects have been simplified or omitted. Those skilled in the art will appreciate variations from these implementations that fall within the scope of the invention. Those skilled in the art will also appreciate that the features described above can be combined in various ways to form multiple implementations. As a result, the invention is not limited to the specific implementations described above, but only by the claims and their equivalents.

Reference has been made throughout this specification to "one example" or "an example," meaning that a particular described feature, structure, or characteristic is included in at least one example. Thus, usage of such phrases may refer to more than just one example. Furthermore, the described features, structures, or characteristics may be combined in any suitable manner in one or more examples.

One skilled in the relevant art may recognize, however, that the examples may be practiced without one or more of the specific details, or with other methods, resources, materials, etc. In other instances, well known structures, resources, or operations have not been shown or described in detail merely to observe obscuring aspects of the examples.

While sample examples and applications have been illustrated and described, it is to be understood that the examples are not limited to the precise configuration and resources described above. Various modifications, changes, and variations apparent to those skilled in the art may be made in the arrangement, operation, and details of the methods and systems disclosed herein without departing from the scope of the claimed examples.

What is claimed is:

1. A waveguide for ultrasonic testing of a wooden specimen, comprising:
   a mating portion configured for interfacing with a transducer horn of an ultrasonic transducer, wherein the mating portion comprises a contact well recessed below a surface of the mating portion and configured to enable a connection between the transducer horn and the waveguide; and a body portion that is fabricated out of metal and extends from the mating portion, wherein the body portion comprises:
a proximal end attached to the mating portion; and
a distal end comprising a contact face orthogonal to the body portion, wherein the contact face comprises a planar surface which lies on a surface of the wooden specimen without penetrating the surface of the wooden specimen and transmits an ultrasonic signal during the ultrasonic testing, and wherein a surface area of the contact face is larger than a cross-sectional area of the body portion.

2. The waveguide of claim 1, wherein the waveguide is fabricated to generate a pre-determined resonance frequency that is optimal for non-destructive evaluation (NDE) of the wooden specimen.

3. The waveguide of claim 1, wherein the contact face is circular, and wherein a diameter of the contact face is larger than a diameter of the body portion at the mating portion to increase a contact area, wherein the contact area comprises an area of the surface of the wooden specimen that is in contact with the contact face of the body portion.

4. The waveguide of claim 1, wherein a shape of the contact face of the body portion is selected from a group that comprises a circle and a polygon.

5. The waveguide of claim 1, wherein the contact well is circular in shape and forms an opening in the surface of the mating portion through which to receive the transducer horn.

6. The waveguide of claim 1, wherein one or more side walls of the contact well are tapped to enable a threaded connection with the transducer horn.

7. The waveguide of claim 5, wherein a diameter of the contact well is sized according to a diameter of the transducer horn.

8. The waveguide of claim 1, further comprising an interfacing component for securing the ultrasonic transducer to the waveguide, wherein the interfacing component comprises:
a front face comprising an aperture, wherein the aperture is sized to receive the transducer horn;
a back face comprising an opening, wherein the opening is open to an edge of the back face and is sized to receive the body portion of the waveguide; and
a gap between the front face and the back face, wherein the gap is sized to receive the mating portion of the waveguide;
wherein the front face and back face are connected along one or more edges.

9. The waveguide of claim 1, wherein the body portion is fabricated with an activatable adhesive to aid attachment of the contact face to the surface of the wooden specimen.

10. The waveguide of claim 2, wherein the pre determined resonance frequency is determined based at least on a wood species of the wooden specimen.

11. The waveguide of claim 1, wherein the distal end of the waveguide is detachable allowing an interchanging of different contact faces for a non-destructive evaluation (NDE) of the wooden specimen.

12. The waveguide of claim 1, wherein the planar surface comprises a flat surface, and wherein the planar surface comprises a radiating aperture.

13. An apparatus for assisting non-destructive evaluation (NDE) of a wooden specimen, comprising:
a waveguide for ultrasonic testing of the wooden specimen, wherein the waveguide comprises:
a mating portion configured for interfacing with a transducer horn of an ultrasonic transducer, wherein the mating portion comprises a contact well recessed below a surface of the mating portion and configured to enable a connection between the transducer horn and the waveguide; and
a body portion that is fabricated out of metal and extends from the mating portion, wherein the body portion comprises:
a proximal end attached to the mating portion; and
a distal end comprising a contact face orthogonal to the body portion, wherein the contact face comprises a planar surface which lies on a surface of the wooden specimen without penetrating the surface of the wooden specimen and transmits an ultrasonic signal during the ultrasonic testing, and wherein a surface area of the contact face is larger than a cross-sectional area of the body portion; and
the ultrasonic transducer.

14. The apparatus of claim 13, wherein the waveguide is fabricated to generate a pre-determined resonance frequency that is optimal for non-destructive evaluation (NDE) of the wooden specimen.

15. The apparatus of claim 13, wherein the planar surface comprises a flat surface, and wherein a shape of the contact face is selected from a group that comprises: a circle and a polygon.

16. The apparatus of claim 13, further comprising: an interfacing component for securing the ultrasonic transducer to the waveguide, wherein the interfacing component comprises:
a front face comprising an aperture, wherein the aperture is sized to receive the transducer horn;
a back face comprising an opening, wherein the opening is open to an edge of the back face and is sized to receive the body portion of the waveguide; and
a gap between the front face and the back face, wherein the gap is sized to receive the mating portion of the waveguide;
wherein the front face and back face are connected along one or more edges.

17. The apparatus of claim 13, wherein the distal end of the waveguide is detachable allowing an interchanging of different contact faces for a non-destructive evaluation (NDE) of the wooden specimen.

18. A method of manufacturing a waveguide for ultrasonic testing of a wooden specimen, comprising:
fabricating, from one or more metallic components, a mating portion configured for interfacing with a transducer horn of an ultrasonic transducer, wherein the mating portion comprises a contact well recessed below a surface of the mating portion and configured to enable a connection between the transducer horn and the waveguide; and
fabricating, from the one or more metallic components, a body portion extends from the mating portion, wherein the body portion comprises:
a proximal end attached to the mating portion; and
a distal end comprising a contact face orthogonal to the body portion, wherein the contact face comprises a planar surface which lies on a surface of the wooden specimen without penetrating the surface of the wooden specimen and transmits an ultrasonic signal during the ultrasonic testing, and
wherein a surface area of the contact face is larger than a cross-sectional area of the body portion.

19. The method of manufacturing of claim 18, wherein the fabricating of the body portion comprises forming the contact face of the body portion in a shape selected from a group that comprises: a circle and a polygon.

20. The method of manufacturing of claim 18, wherein the waveguide is fabricated to generate a pre-determined resonance frequency that is optimal for non-destructive evaluation (NDE) of the wooden specimen.

\* \* \* \* \*